US010244965B1

(12) United States Patent
Gibson

(10) Patent No.: US 10,244,965 B1
(45) Date of Patent: Apr. 2, 2019

(54) CAPNOGRAPHY DEVICE WITH CONSTANT REMOTE SURVEILLANCE AND NOTIFICATION CAPABILITIES COUPLED WITH AUTOMATED DRUG DELIVERY INSTRUMENTS

(71) Applicant: Jeffrey S. Gibson, Fort Smith, AR (US)

(72) Inventor: Jeffrey S. Gibson, Fort Smith, AR (US)

(*) Notice: Subject to any disclaimer, the term of this patent is extended or adjusted under 35 U.S.C. 154(b) by 0 days.

(21) Appl. No.: 16/109,794

(22) Filed: Aug. 23, 2018

Related U.S. Application Data

(63) Continuation-in-part of application No. 15/912,111, filed on Mar. 5, 2018, now Pat. No. 10,080,498.

(51) Int. Cl.
| | |
|---|---|
| *A61B 5/08* | (2006.01) |
| *A61B 5/083* | (2006.01) |
| *A61M 5/172* | (2006.01) |
| *A61M 16/00* | (2006.01) |

(52) U.S. Cl.
CPC ......... *A61B 5/0836* (2013.01); *A61M 5/1723* (2013.01); *A61M 16/024* (2017.08); *A61M 2202/0482* (2013.01); *A61M 2205/18* (2013.01); *A61M 2205/3584* (2013.01); *A61M 2205/3592* (2013.01); *A61M 2205/50* (2013.01); *A61M 2205/60* (2013.01); *A61M 2230/432* (2013.01)

(58) Field of Classification Search
CPC combination set(s) only.
See application file for complete search history.

(56) References Cited

U.S. PATENT DOCUMENTS

| | | | | |
|---|---|---|---|---|
| 9,782,084 | B2* | 10/2017 | Maertz | A63B 24/0062 |
| 9,980,140 | B1* | 5/2018 | Spencer | G06F 21/629 |
| 2003/0106553 | A1 | 6/2003 | Vanderveen | |
| 2005/0177096 | A1* | 8/2005 | Bollish | A61B 5/02055 604/65 |
| 2009/0076461 | A1* | 3/2009 | Susi | A61M 5/14228 604/246 |
| 2009/0209849 | A1* | 8/2009 | Rowe | A61B 5/06 600/424 |
| 2011/0066061 | A1 | 3/2011 | Colman et al. | |
| 2013/0253336 | A1* | 9/2013 | Haveri | A61B 5/082 600/476 |

(Continued)

*Primary Examiner* — Eric J Messersmith
(74) *Attorney, Agent, or Firm* — William S. Parks

(57) ABSTRACT

A completely wireless capnography/drug delivery system is provided, with the drug delivery device reacting in relation to raw data transfers from the capnography device. Such a system utilizes the same capnography waveform generating algorithm within each component device (including an external connectivity base and a possible data center, as well) to receive raw data for comparison waveform results to ensure system functionality and to prevent outside data compromise or hacking. If an alert as to subject patient capnography waveform results initially at the capnography device, the other system component devices are alerted and such raw data is then transferred for such mirror capnography waveform generation at each location. Such a system thus allows for the drug delivery device to provide needed drug delivery operations directly, and wirelessly, in relation to such capnography waveform results, allowing the subject patient full mobility while monitored and treated.

8 Claims, 5 Drawing Sheets

(56) References Cited

U.S. PATENT DOCUMENTS

| | | | |
|---|---|---|---|
| 2013/0324873 A1* | 12/2013 | Babaeizadeh | A61B 5/0836 600/532 |
| 2015/0101600 A1* | 4/2015 | Miller | A61M 16/16 128/202.22 |
| 2015/0238722 A1* | 8/2015 | Al-Ali | A61B 5/0836 128/205.13 |
| 2016/0313290 A1* | 10/2016 | Forzani | A61B 5/082 |
| 2017/0007159 A1* | 1/2017 | Dieffenderfer | A61B 5/087 |

* cited by examiner

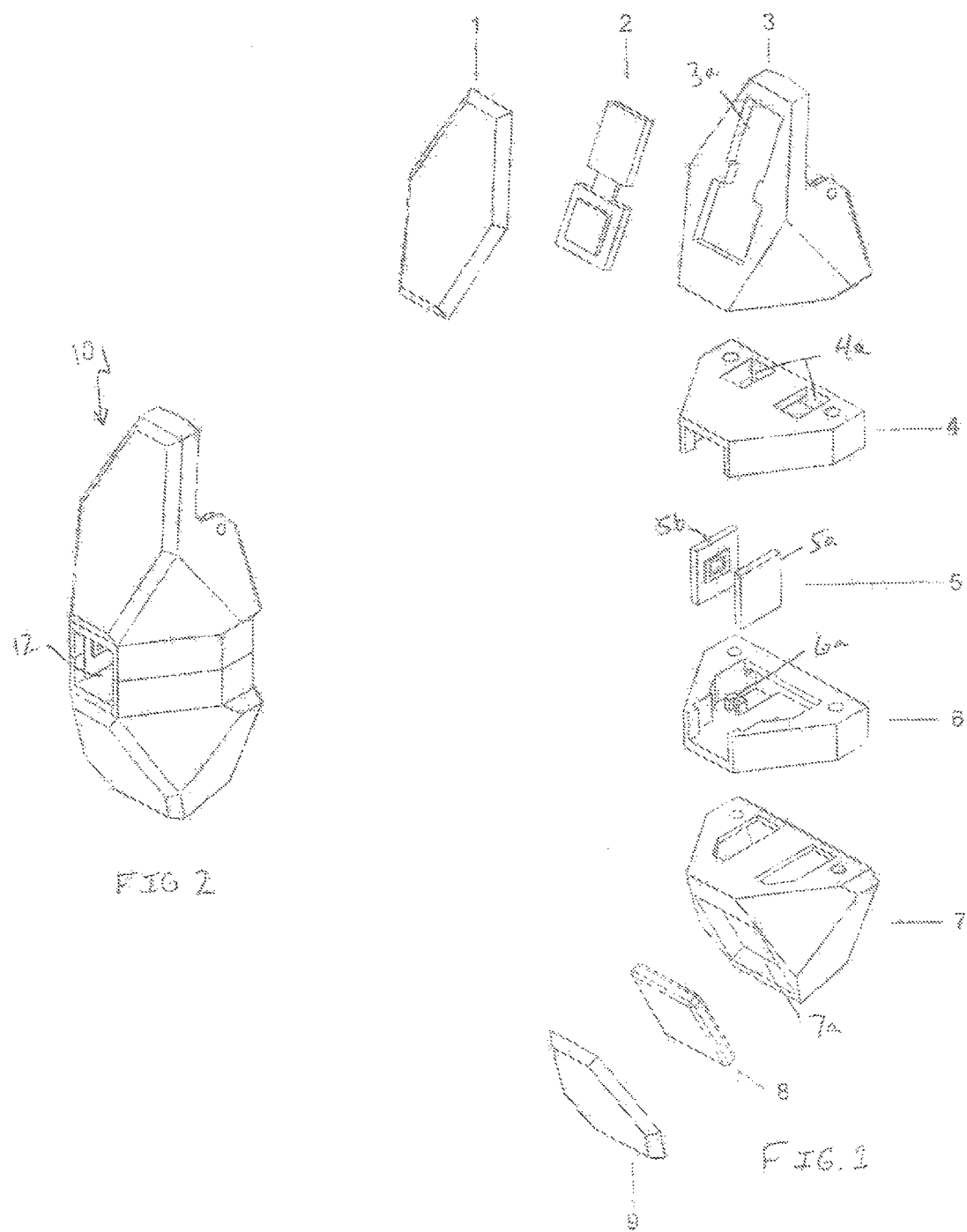

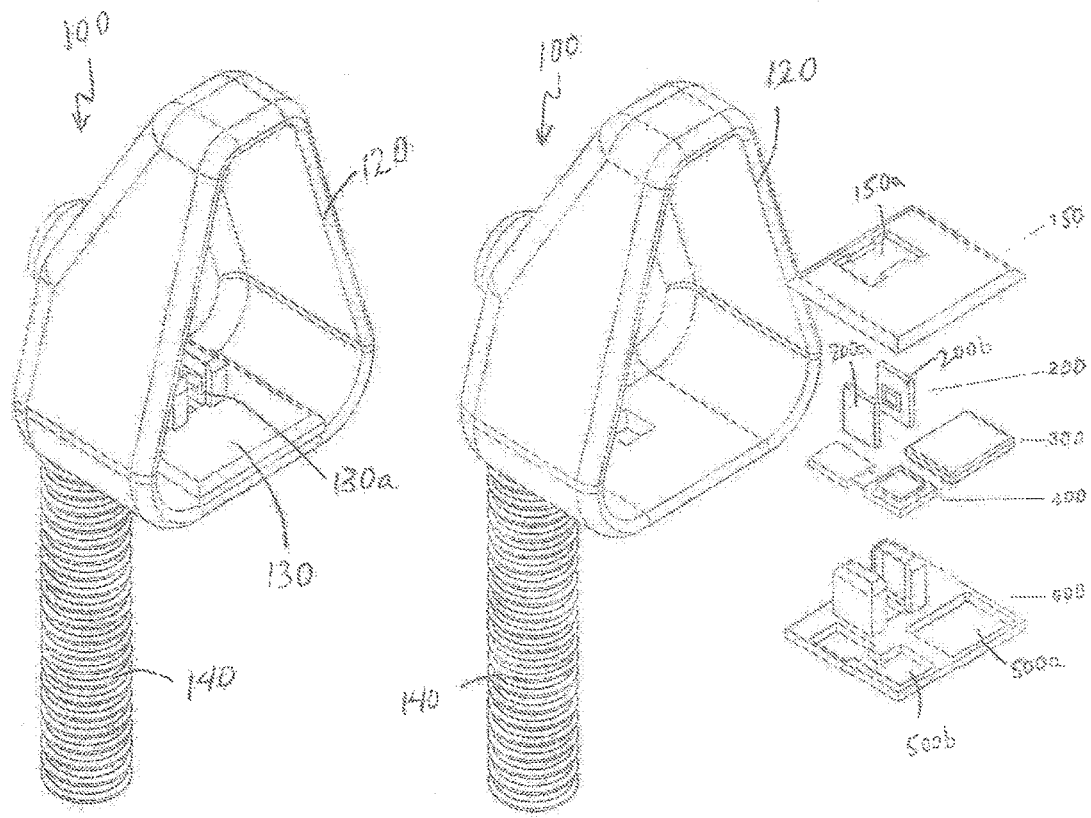

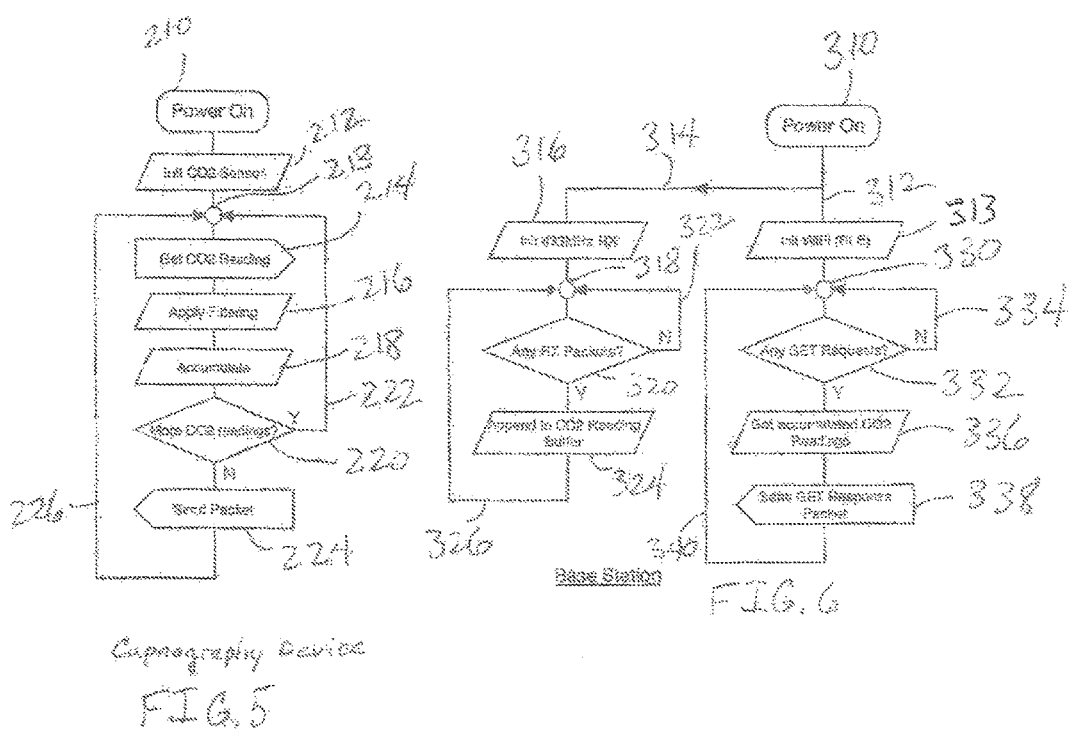

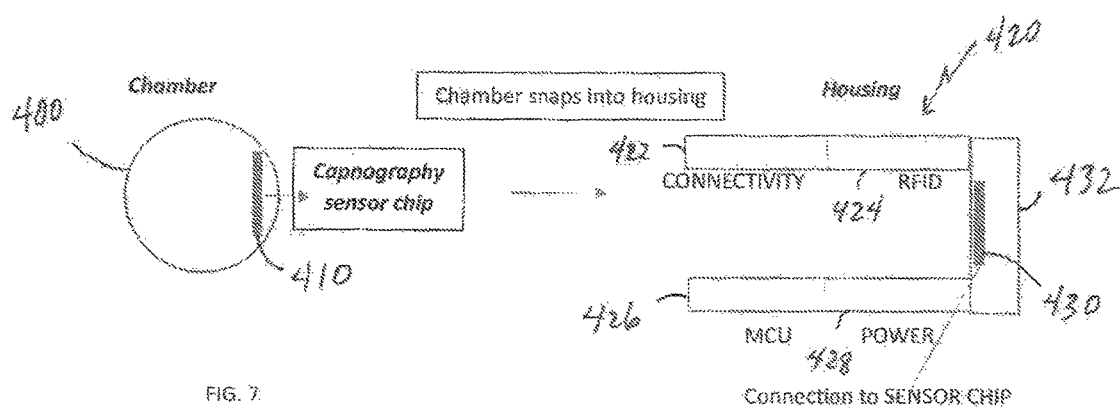

CAPNOGRAPHY DEVICE WITH CONSTANT REMOTE SURVEILLANCE AND NOTIFICATION CAPABILITIES COUPLED WITH AUTOMATED DRUG DELIVERY INSTRUMENTS

CROSS-REFERENCE TO RELATED APPLICATION

This application is a continuation-in-part of copending U.S. patent application Ser. No. 15/912,111, filed on Mar. 5, 2018, the entirety thereof is herein incorporated by reference.

FIELD OF THE INVENTION

The present invention relates to a capnograph including a suitable sensor to measure carbon dioxide concentration for a target patient (or other individual). Such a device utilizes at least one microprocessor (MCU) to govern overall activation and communication between the capnograph and ultimately a data center. Such a component is provided with at least one RFID tag in order to charge device and transfer data via inductive coupling and to use as a device ID for data routing purposes. The utilization of RFID, Bluetooth, WIFI, cellular, and MCU components allows for collection and transfer of reliable data. Coupled with a multi-faceted communication system, with variable options of utilizing an RFID reader, wi-fi, Bluetooth, cellular, and any other type wireless communication platform, the capnograph permits immediate notifications to various entities and effective data transfer to a data center for eventual processing (within, as one non-limiting example, a secure cloud). The MCU may thus provide pre-programmed information to determine alert levels for a target patient, with the utilization, additionally of a data recordation device (like an SD card, for example) to capture all sensor results for such a target patient as well. If an alert occurs, the MCU triggers communication via one of the previously noted data transfer methods and transfers all subsequent information from the sensors to the data center through any or possibly all alternative communication pathways. An inductive coupling component within the connectivity base allows for both powering up and instantaneous data transfer on demand, as well. Thus, the inventive device and system provides a real-time, reliable, wireless surveillance and notification platform that has been lacking in the industry.

Additionally, the wireless capnography system is incorporated within a drug delivery system in relation to drugs/medicaments (pharmaceuticals, gases, antidotes, and the like) associated with patient conditions pertaining to capnography monitoring and measurements. Such an overall system utilizes the same capnography waveform generating algorithm as present within the capnography device, the external connectivity base, and the data center, allowing for raw data transfer to each algorithm from the capnography device and, subsequent to confirmation of proper raw data receipt, generation of comparative capnography waveforms, after the capnography device indicates waveform results falling outside of subject patient parameters. In such an instance, the drug delivery device, having the same capnography waveform generating algorithm present within its operating system (since such a delivery device, such as a programmable pump, ventilator, ventilating assistance device, and the like, includes its own microprocessor, or like computer instrument), receives notification of alarm codes from the capnography device permitting such uniform waveform generation and subsequent analysis thereof to determine levels of drug/medicament necessary for treatment of the subject patient in response to such a capnography measurement situation. Furthermore, such a system allows for a pre-set time interval (separate from random alarm generation) for planned raw data bursts to the drug delivery device operating system algorithm (as well as external connectivity base and, if needed and present, data center) in order to assess the proper function and operation of the overall system itself. With such a system, there is provided a complete patient assessment and drug delivery process with an all wireless, even wearable, capability. Heretofore, such a system has yet to be developed or workable within the healthcare industry.

BACKGROUND OF THE PRIOR ART

Respiratory concerns have always been of significant interest within the medical world. Certainly, the lack of sufficient breathing capacity lends itself to various and myriad problems for patients. Whether it concerns chronic obstructive pulmonary disease (COPD), emphysema or other lung maladies (including lung cancer and resultant issues), asthma, allergies, failures of internal respiratory cycles, or even, to a more specific level, sudden infant death syndrome and its unknown causes, there has been a long-standing need to understand and, more importantly, develop proper treatment for such breathing problems. In particular, the ability to actually continuously and reliably monitor a subject patient's capability of expelling sufficient carbon dioxide levels (in relation, for instance, to the amount of oxygen inhaled) to indicate appropriate respiratory levels has been a significant concern.

Capnography is considered the measurement of the level of carbon dioxide ($CO_2$) in relation to a patient's respiratory status. Infrared sensors have been typically utilized for such a purpose, particular since carbon dioxide absorbs infrared light particularly well. Thus, typically, capnographs measure infrared absorption within a patient's exhalation profile to determine the rate of carbon dioxide generation and/or expulsion as an indicator of patient ventilation and thus respiratory effectiveness. The information obtained from a capnographic measurement is sometimes presented as a series of waveforms representing the partial pressure of carbon dioxide in the patient's exhaled breath as a function of time. Such a measurement is not easily rendered, however, through the standard devices utilized today, at least in terms of definitive data integrity and reliability thereof. However, for monitoring purposes, capnography is considered to be a prerequisite for safe intubation and general anesthesia, as well as for correct ventilation management in other areas.

Capnographs are typically utilized in conjunction with the delivery of medicinal gas, oxygen, for instance, to treat certain breathing disorders. Oxygen (and like) masks are the preferred method of such delivery, whether to cover the subject patient's mouth or to deliver through cannulae within his or her nostrils, or both nose and mouth in terms of coverage and delivery (and, for that matter, receipt of exhaled carbon dioxide, as well). Such a pathway allows for inhalation and exhalation as needed for delivery of treatment (medicinal) gas and expulsion of the resultant carbon dioxide from the patient's respiratory system. Whether through an all-encompassing (mouth and nose covering, for example), mouth alone, or nose alone, such a method employs fluidic gaseous transport for such a purpose.

With these types of devices, in any event, there have been implemented, as noted above, capnography devices to monitor certain gas measurements in relation to such treatments. These prior devices are, however, limited in that they are typically provided within the gas line as a rather sizeable structure and generally capture momentary, and not continuous, results in such a manner. Likewise, as noted herein, such devices are connected through expensive cables (which are susceptible to breakage, downtime, and replacement at significant cost) that lead to a monitoring record device that itself is of significant cost and relies upon the reliability of the worn device, the cable connector, and the machinery therein itself to provide correct readings in relation to the measurements collected at the worn device level. Such devices, thus, if needed for any type of continuing monitoring purpose, must be moved with the subject patient. These devices, requiring a directly cable-connected monitor is extremely limited in terms of mobility, for obvious reasons, as the monitoring record device itself weighs a number of pounds, at least, and requires carrying if the patient requires continuous connection thereto. Even movement from, for example, a hospital bed to a restroom requires significant and cumbersome choreography lest the system be disconnected and then reconnected thereafter. If the patient desires greater mobility, or even desires the ability to utilize such a device at his or her home, either disconnection (when such connection is paramount for monitoring purposes, of course, at least potentially) or significant mobility configurations and actions would be necessary. Such is particularly necessary due to the rather delicate nature of such monitoring record devices; dropping such devices at any height could compromise if not disrupt entirely (for that matter, break) the capabilities of the record device to the extent that it is no longer useful and replacement (again, at significant cost) is needed. The same could be said for the cable connection as any rigorous activity undertaken in relation to such a component could effectively compromise its usefulness as well. And, as above, excessive costs are associated with such connection components if replacement is of necessity. In other words, then, the current state of the capnography art is limited significantly to such large, cumbersome, low-mobility (if at all) devices. Coupled with the fact that such a capnograph itself is typically rather large and connected to the breathing lines themselves, the care needed to ensure such a base device does not break during any activities would be of vital importance, as well. There exists a definite need to supplant such current devices, if not the entire system itself, to allow for greater mobility of patients, at least, and to permit improved measurement results, as well. The further ability to utilize data of great integrity in relation to such capnographic measurements, if not in terms of continuous, reliable results, for notification purposes as well as possible reliable predictive health status modeling, would be of significant extra benefit, too.

The current state of capnography devices and methods, unfortunately, as alluded to above, leaves much to be desired, particularly in terms of costs, limited monitoring intervals, cumbersome requirements in terms of potential mobility for a patient, and, perhaps most importantly, the lack of remote capabilities and, as a result, the inability to monitor multiple users through one data center simultaneously (and, furthermore, the lack of any real-time capabilities to provide predictive modeling for treatment potentials for such patients). In other words, the current methods employ capnograph devices that are provided along an oxygen line and record, within the confines of a "box" structure that itself is connected through at least one cable to an outside monitoring recorder for actual review of the patient's measured levels. Such a connection is made through a rather expensive cable (wire/cord) and the monitoring record device is limited to that specific patient and, perhaps more importantly, is provided itself within a rather large, heavy, and breakable structure. Although such a "standard" capnography system used nowadays has some degree of reliability for monitoring purposes, it remains problematic that such a device limits the range of mobility for a patient, at least. However, another particular important issue concerns the fact that such a current standard system also is limited to one capnograph per one monitoring device; there are no remote data processing capabilities that allow for a database to handle such capnogram data from multiple patients simultaneously. Additionally, however, the lack of provision of such a device within a smaller, confined area, let alone through a reliable transfer protocol other than via a cable that may fail or at least become damaged and require replacing is another significant drawback of such a "typical" system.

Additionally, the current capnograph technology does not provide any benefits that would be certainly of great interest for a potentially automated and fully enclosed system. There is lacking any definitive capability for on-line and automatic systems checks in order to ensure the entire device is functioning properly, both in terms of actual data capture capacity and data transfer realities. Likewise, there is no means provided within the state of the capnography art to accord definite date and time stamp data for captured and transferred data packets; at best, such systems merely capture data on the fly and send the same to a cable-connected single-person data base. There is nothing within the prior art disclosing a multi-patient capability with full data integrity capture, transfer, and back up. Furthermore, the current systems do not lend themselves to any predictive modeling potentials, wasting an opportunity to capture certain patient vital information that may be utilized to establish a future estimate as to such a specific patient's condition and suitable suggested treatment in relation thereto. In essence, the data related to the patient's respiratory levels (capnogram and/or waveform) are not provided in a sufficiently reliable manner and with such integrity as to permit such a predictive model to be established with any precision, at least not enough for risk-taking with such an artificial intelligence platform. Thus, there remains a noticeable need for such beneficial results within this specific medical realm, which the current monitoring systems are clearly lacking. The present invention provides such benefits and overcomes the deficiencies of the state of the capnography art.

Of particular difficulty has proven the potential for a system that not only allows for capnography measurements, but also utilizes such results for a reliable and direct operation of a drug delivery device in relation to such capnography measurements, specifically with such a system operated wirelessly between every component. There have been suggested wireless capnography devices in the prior art, albeit solely in terms of captured results within a single device, not in terms of utilizing more than one with the same waveform generating algorithm. There have also been suggested systems wherein a capnography device is utilized to transfer results to a drug delivery device for delivery purposes in response to such results. These systems, however, are limited to hospital or like room settings and typical delivery devices in place (such as IV towers, wall-mounted gas tank feeders, and the like). Likewise, such systems rely upon measured results primarily, not upon mirrored algorithms at different devices to ensure such capnography data is reliable and proper (or to ensure the system is actually operating properly itself). As such, these prior art systems lack the ability to, for instance, prevent outside hacking or other like possible detrimental situations since the results are developed at the capnography device itself or through a single algorithm location, lacking a means to ensure such data is proper and not compromised. To that end, the lack of such reliability lends itself to further difficulties in correlating drug delivery reliant upon such potentially suspect results, as well. As such, as noted above, these prior art systems have only been pondered, not integrated within the health industry. The present invention overcomes all of the prior deficiencies and problems associated with these earlier concepts.

Advantages and Summary of the Invention

One significant advantage of the present inventive capnograph is the potential for a miniature size thereof and the ability to integrate the same within a standard gas transport line for receipt of exhaled gases. Another advantage is the ability of such a device, at whatever size, to provide a continuous monitoring platform through cyclic acquisition of data allowing for the generation of specific date and time stamps related to system power up and data capture for reliability and security purposes. Another advantage is the overall capability of such a system to provide high integrity data for predictive modeling purposes at a level heretofore unavailable within this area. Yet another advantage is the capability of remote data transfer from a plurality of capnographs to a single data center for analysis and compiling purposes as desired, basically providing scalability for a widespread system for constant, reliable monitoring purposes and immediate notifications if necessary (not to mention the potential to compare and consider similar patient characteristics and recorded results for predictive modeling purposes within the same data center platform, as well). Still another advantage of this system is the utilization of programmed hardware components coupled with RFID tags, Bluetooth, WIFI, and/or cellular components for fully integrated and safe and reliable and low power transfer of information and programming of the MCU on the fly if needed. A further advantage is the ability of the overall system to provide an initial alert protocol in relation to a target patient's breathing status with the added capability of autodirection by an MCU component to generate streaming of such patient's subsequent capnograph status through any communication protocol (wi-fi, Bluetooth, RFID reader, etc.) to a monitoring data center, as well as automatically communicating with the patient, emergency responders, or physician (and others as suitable and/or as needed), simultaneously with such alarm streaming, with the additional capability of transferring raw data from the capnography device to any other receiver for compilation of verified information into recorded waveforms pertaining to such a patient/individual's respiration status. Yet another distinct advantage is the utilization of a mirrored algorithm at the MCU, the connectivity base, and within the data center to provide a mechanism for individual system component checks and to compile and generate a waveform in relation to the data from the IR sensor pertaining to voltage differentials due to $CO_2$ level measurements wherein the MCU provides a monitoring result for notification and alarm purposes and the data center provides an archival result for analysis, diagnosis, and other possible review purposes. And yet another advantage is the ability to provide such a device as a small profile structure as small as a miniaturized smart sensor within a properly aligned and configured housing to direct and capture sufficient amounts of exhaled gases from a target individual in order to provide a device that may be employed and deployed in a noninvasive manner (for comfort, reliability, durability, and versatility, at least) and in relation to any environment as needed (surgical operating room, CPAP mask, SCUBA mask, vehicle driver headset, pilot headset, etc.). The MCU component contained within the capnography device itself exhibits the capability for patient/individual data and status based upon data trends within a single 24-hour time period secondary to data storage limitations based upon both space and power capacity therein. The capnography algorithm held within the data center permits construction of a suitable waveform from generated, stored, and transferred data from the device and/or connectivity base. In this manner, the data center provides the ability for patient data and status to be evaluated based upon much longer time periods secondary, again, to the capacity of memory space and power limitations of the capnography device itself. Still a further advantage of the disclosed system is the ability to provide a triple benefit through inductive coupling of the capnograph with a connectivity base station, wherein physical placement of the capnograph on such a device at the connectivity base generates power supply levels therein, simultaneously transfers rough IR sensor data held within a capnograph data storage chip and/or MCU, for compilation and waveform generation at the data center and other locations as needed, and also provides programmed directions/modifications for the MCU within the capnography device to change cycle parameters for further data generation and capture. Yet another advantage of the disclosed system is the capability to provide automated systems checks for the device in addition to monitoring the patient/individual's respiratory status, thereby allowing for a device that can be utilized in any location with reliable data in a continuous manner. Even further as a significant advantage of the disclosed invention herein is the ability to introduce the same capnography waveform generating algorithm within the operating system of a drug delivery device (programmable pump, programmable ventilator, programmable ventilating assistance device, and the like) that is earlier coupled through a prior drug delivery device instituted Bluetooth, Wi-fi, or other potential communication pathway [provided ostensibly to transfer information directly to an external electronic medical record (EMR) system] in order to couple the base capnography system with such a drug delivery component. Another advantage is the transfer of raw capnography data to such a drug delivery operating system algorithm (and external connectivity base and data center algorithm, simultaneously) to allow for capnography waveform generation at each device for separate and comparative alarm code generation within the different system components in order to establish the raw data is uniform and not compromised when transferred to any individual system device. Yet another advantage is the ability to reserve significant amounts of power through monitoring at the capnography device for patient results that are outside required capnography parameters, with any transfer to the other system devices undertaken in relation to an alarm of improper capnography measurements from the capnography device algorithm. Additionally, another advantage of this full capnography/drug delivery system is the ability to utilize raw data bursts at set intervals to retain lower power levels but still determine if the entire system devices are functioning properly.

Accordingly, the inventive system encompasses a capnography monitoring, notification, and analysis system comprising a) a capnography device having a patient (or other individual, such as, without limitation, a firefighter, airline pilot, scuba diver, etc.) exhalation capture passage, an infrared source providing an infrared beam through said passage, an infrared sensor aligned opposite said infrared source to detect infrared measurements associated with carbon dioxide concentrations within a patient's captured exhalation, a microcomputer, at least one RFID tag, an optional data storage component other than said microcomputer, and a communication component including a WIFI antenna, a blue-tooth antenna, and, optionally, a cellular communicator, b) an external connectivity base comprising an inductive coupling component, a receiver component for reception of communicated information from said capnography device, a mirrored algorithm (e.g., an exact duplicate of the device MCU algorithm), and an information transfer component, and c) a data center comprising a rules engine, a mirrored algorithm (as above, again, an exact duplicate of the device MCU algorithm), and a computer processor;

wherein said capnography device, said base station, and said data center include the same algorithm for compiling infrared sensor measurements from said infrared sensor to generate a capnograph waveform associated therewith, wherein said MCU of said capnography device further includes pre-set parameters associated with certain maximum and minimum carbon dioxide measurement levels, inspiration length measurement durations, and expiration length durations as captured by said infrared sensor and compiled by said algorithm in a waveform, wherein if at any time during utilization by a patient (or other individual), said parameters are exceeded in terms of said maximum or below said minimum carbon dioxide levels for a pre-set continuous amount of time, then said microcomputer generates an alarm for communication with said external connectivity base through any or all of said communication possibilities such that said external reader provides immediate notification to pre-selected parties as to the condition of said patient in relation to said exhalation carbon dioxide measurements, wherein, upon such a notification result, said capnography device continues to capture carbon dioxide exhalation measurements with transfer from said MCU in noncompiled state to at least one communication component of said at least one RFID tag, Bluetooth antenna, WIFI antenna, and/or cellular communicator, for continuous transfer to either said external connectivity base thereafter and subsequently to said data center, or, alternatively, directly to said data center, and said MCU further generates an alarm code within said algorithm therein as an indicator of the situation pertaining to said alarm generation, wherein said transfer to said base station and/or said data center is undertaken for transfer of the alarm situation whether in terms of patient/individual respiratory status or capnography device status via compilation of said transferred raw data within said mirrored algorithm and verification and processing thereof; and wherein said capnography device further receives power from and transfers information directly to said external connectivity base through said inductive coupling component upon placement of said capnography device within a certain proximity thereto said external connectivity base; wherein said inductive coupling capability further provides raw data transfer and alarm notification to said base station upon discovery of defect within said capnography device for possible remedy thereof.

Additionally, such an invention encompasses a device having a physical housing, at least one microprocessor unit including an internal clock, at least one sensor originating source component (with up to 5 per each microprocessor unit present), at least one measuring sensor (with up to 5 per microprocessor unit present), wherein at least one programmed MCU is present to control activation of said sensor source(s) and said sensor(s); wherein said at least one microprocessor unit (MCU) is programmed with at least one algorithm to create a capnography waveform from data received from said at least one sensor; at least one component to receive formatted data from the MCU and transfer received data to an external connectivity base and/or data center, said component being either i) a RFID tag to transfer such data to an external RFID reader imbedded within said connectivity base, or ii) a NFC tag and antennae to transfer such data to an external NFC reader, (if so, then such NFC tag being compliant with and utilizing the ISO/IEC 15693 standard); at least one power supply; and external communication capabilities associated with wireless, WIFI LAN, Bluetooth, cellular, and/or RFID reader information transfer;

wherein said sensor source and said sensor are configured appropriately and aligned for emission of a beam or like result directly towards said sensor for measurement of a subject measurable article, level, dimension, condition, and the like; wherein said microprocessor unit is connected to said sensor to permit transmission of data from said sensor to said microprocessor unit; wherein said MCU includes a flash memory component that is formatted to receive said sensor-transmitted data; wherein said MCU includes a program (such as an algorithm, as one example) to process said raw data from the sensor and convert the same into an appropriate capnography format for patient status evaluation based upon preset limits (maximum and minimum) in order to provide parameters to trigger the alarm function; wherein said MCU includes a program to format said sensor transmitted data for proper transmission via Bluetooth, WIFI LAN, and cellular, wherein said MCU further includes a program to write sensor data onto a data storage chip built into said capnography device, wherein said MCU further exhibits the ability to write said received sensor data onto said RFID tag or said NFC tag; wherein said RFID or NFC tag is programmed to receive an interrogation from a suitable external connectivity base device, said interrogation and programmed status permitting transfer of the data received from said MCU to said external reader; wherein said power supply, if present, continuously provides electrical power to said sensor source, said sensor, and, possibly, said MCU; wherein said sensor source and said sensor are activated by said MCU, wherein said MCU thereby acts to permit transmission of power from said power supply to said source and said sensor; wherein said sensor generates data from the emission leading therefrom said source to said sensor; wherein said data generated by said sensor automatically transmits to said MCU; wherein said MCU is programmed to receive said data and to deactivate said sensor and said source at a set time interval in relation to said internal clock, thereby limiting the actual amount of data transmitted by and received from said sensor; wherein said MCU stores all transferred information from said sensor within its flash memory and/or within said capnography device data storage chip; wherein said MCU automatically formats and transfers all received and stored information to said capnography device data storage chip, unless preset alarm limits are exceeded then said MCU writes alarm code and alarm data to said RFID or NFC tag, and further activates Bluetooth, WIFI LAN, and or cellular transmission systems imbedded within said capnography device to achieve connectivity through the most efficient available connection for continuous data streaming at that moment; wherein the presence of a viable connection immediately starts said device alarm data streaming and powers down all other methods not being utilized, and writes alarm code to said RFID and/or NFC tag; wherein said MCU is programmed to stop receipt of information from said sensor and power down both said source and said sensor in evenly timed intervals, whereupon said MCU transfers said information to write upon said capnography device data storage chip; wherein said RFID or NFC tag sends all received information from said MCU to said external connectivity base upon each data call and inductive coupling process initiated by placing said capnography device directly upon said RFID reader embedded in said connectivity base; wherein said suitable external connectivity base device base station transfers all received information from said at least one RFID or NFC tag, or Bluetooth, WIFI LAN, or cellular transmission to said data center; and wherein the total size of said housing is low-profile. Additionally, the invention also encompasses a method of providing continuous surveillance and external notifications for a target audience in relation to a status and condition monitored by a device, said method including the steps of: providing a device (as noted above); providing an external connectivity base attuned for transmission of signals to and receipt of data from said RFID or NFC tag and capnography device Bluetooth, WIFI LAN, and or cellular communication components; providing a data center external to both said external connectivity device base station and said device, said data center attuned with said external connectivity base device base station to receive data transmitted from said external connectivity base via said RFID or NFC tag thereto, and said data center including at least one mirrored algorithm in relation to the algorithm present within said capnography device and/or rules engine to analyze and act upon said received data; introducing said device within a proximate distance of the item to be monitored; to transmit any data written thereon to said external connectivity base and simultaneously causing said MCU to directly activate said electrical signal; receiving samples for monitoring within or proximal to said device wherein said activated source provides said emission to said activated sensor within and/or proximate thereto said monitored item is present and measured by said source, in relation to fluctuations of voltage measured thereby; transferring said captured measurement data from said activated sensor to said MCU, said transmission of data causing said at least one MCU to receive said data and to subsequently indicate deactivation, thereby causing said source and said sensor to power down until reactivated by said MCU, wherein said MCU remains activated for receipt of data, but is limited to such data transmitted by said activated sensor, wherein said transmitted data is stored within said flash memory of said MCU; formatting of said transmitted data stored within said flash memory to a suitable language for transmission and writing on said RFID or NFC tag and/or said capnography device data chip; transmitting said formatted data from said at least one MCU either to said RFID or NFC tag or directly to said connectivity base or directly to said data center through wireless, Bluetooth, and/or cellular signal from said MCU; wherein if said signal (alarm code) is sent through either via said RFID or NFC tag, such is communicated to said external connectivity base in response to a subsequent data call and upon receipt of said alarm code from either of said RFID or NFC tag to said external connectivity base without prior connectivity of any of the other communication avenues (wi-fi, Bluetooth, cellular, etc.), then said communication between said capnography device and said external connectivity base is undertaken by one of said other communication avenues as is easiest to achieve (e.g., first to connect with said external connectivity base in such a situation); and repeating each step indefinitely thereafter; wherein said external connectivity base received data is transmitted to said external data center in relation to the identity of the target item associated with said device and said external connectivity base, wherein said external data center may utilize such received data (such as, without limitation, as a capnogram waveform for such a target patient) for continuous comparative review of said target item's standard status for surveillance purposes, wherein any deterioration and/or degradation of such a waveform signal will further allow for target item owner/manufacturer/care provider, etc., notification, emergency notification, or both, dependent upon the severity of any detected deterioration and/or degradation.

The disclosed invention may also encompass a capnography monitoring, notification, analysis, and drug delivery system for an individual person comprising a) a capnography device having an exhalation capture passage, an infrared source providing an infrared beam through said passage, an infrared sensor aligned opposite said infrared source to detect voltage variations associated with carbon dioxide concentrations, inspiration length, and expiration length within said individual's captured respiratory status, a microcomputer (MCU) programmed with a capnograph waveform generating algorithm, at least one radio frequency identification (RFID) tag, an optional data storage component other than said microcomputer, and a communication component including a WIFI antenna, a blue-tooth antenna, and, optionally, a cellular communicator, b) an external connectivity base comprising an inductive coupling component associated with said capnography device, a receiver component for reception of communicated information from said capnography device, a computer processor, and an information transfer component, wherein said external connectivity base computer processor is programmed with the same waveform generating algorithm as the capnography device, c) a data center comprising a rules engine, and a computer processor, wherein said data center computer processor is programmed with the same waveform generating algorithm as the capnography device, and d) at least one drug delivery device having an operating system programmed with the same waveform generating algorithm as the capnography device, wherein said at least one drug delivery device is automated; and wherein said drug delivery device operating system is further programmed with capnography waveform parameters associated with a drug for treatment of a subject patient therewith in relation to said capnography device utilization; wherein said algorithm programmed within said capnography device, said external connectivity base, said data center, and said drug delivery device operating system compiles infrared sensor measurements from said infrared sensor to generate a capnograph waveform associated therewith, wherein said MCU of said capnography device further includes pre-set parameters associated with certain maximum and minimum carbon dioxide measurement concentrations, inspiration length measurement durations, and expiration length measurement durations as captured by said infrared sensor and compiled by said algorithm in a waveform, wherein if at any time during utilization by said individual, said parameters are exceeded in terms of said maximum or below said minimum carbon dioxide concentrations for a pre-set continuous amount of time, then said microcomputer generates an alarm code associated specifically with said waveform measurements for communication for immediate notification to pre-selected parties as to the condition of said individual in relation to said exhalation carbon dioxide concentration measurements, wherein, upon such a notification action, said capnography device continues to capture carbon dioxide exhalation concentration measurements with transfer from said MCU in noncompiled state to at least one communication component of said at least one RFID tag, Bluetooth antenna, WIFI antenna, and/or cellular communicator, for continuous transfer to at least said drug delivery device operating system and said external connectivity base, and, alternatively, also to said data center, and said MCU further generates an alarm code within said capnograph waveform generating algorithm therein as an indicator of the situation pertaining to said alarm generation, wherein said transfer to said drug delivery device operating system and said external connectivity base and/or said data center is undertaken for transfer of the alarm situation whether in terms of patient/individual respiratory status or capnography device status via compilation of said transferred raw data within said capnograph generating algorithm and verification and processing thereof; wherein said drug delivery device operating system is further programmed to provide delivery operation modification of said drug in response to an alarm generation at said capnography device upon transfer, receipt, verification, and processing of said raw data from said capnography device MCU and generation of said waveform by said drug delivery device operating system capnography waveform generating algorithm such that any resultant waveform levels outside said parameters associated with said drug for said subject patient causes a drug delivery operation modification in response thereto, wherein said delivery operation modification is selected from the activities of activating said device, deactivating said device, increasing flow of drug delivery by said device, decreasing flow of drug delivery by said device, increasing concentrations of drug within flow delivery by said device, decreasing concentrations of drug within flow delivery by said device, and any combination or combinations thereof; wherein said capnography waveform generating algorithm located within all of said capnography device, said external connectivity base, said data center, and said drug delivery device operating system receives the same raw data from said IR sensor of said capnography device and thus generates, as needed and upon v, the same capnography waveform at all such locations, allowing for complete comparisons to assure said raw data and said waveform results are proper; wherein said capnography device further receives power from and transfers information directly to said external connectivity base through said inductive coupling component upon placement of said capnography device within a certain proximity thereto said external connectivity base; and wherein said inductive coupling capability further provides raw data transfer and alarm notification to said external connectivity base upon discovery of defect within said capnography device for possible remedy thereof. Such a system may utilize any type of capnography-associated drug delivery device, including, without limitation, a programmable pump, a programmable ventilator, and any combination thereof. Such a drug delivery device may be an internal drug delivery pump attached to a line selected from the group of at least one intravenous line, at least one feeding tube, at least one epidural line, at least one patient-controlled analgesia line, and any combination or combinations thereof. Such a device may also be a programmable ventilator selected from the group a CPAP machine, and a BIPAP machine, and/or a mechanical ventilatory assistance device, and any combination or combinations thereof.

The system functions similarly to that described above in that the data transferred from said IR sensor to said capnography device MCU is provided through each data capture cycle in relation to the time each cycle begins, the time said capnography device MCU receives the data from said infrared sensor, and the amount of data transferred from said infrared sensor to said capnography device MCU for an exact period of time, wherein such provided data is present within a data packet related to each data capture cycle with such specific values for time and amount of data transferred included for verification purposes within said capnograph waveform generating algorithm, wherein if all of said values match the expected values at said data center for each data packet therein received from said base, then said algorithm verifies such data packets are true and allows for further computer processing thereof to form said capnograph waveform for parameter comparisons of the status of said individual's respiratory status in order to monitor for any excess or too low carbon dioxide levels, unacceptable inspiration duration, and/or unacceptable expiration duration, wherein if any parameters fall outside acceptable levels for an excessive time duration then said algorithm generates said alarm code, wherein said alarm code causes certain activities within the overall system to subsequently occur including: a) notification if such data indicates said individual requires immediate attention and/or said device requires remedy for problems or defects therein, b) continuous streaming of collected raw data from said IR sensor to said MCU to pre-selected external locations that utilize the same capnography waveform generating algorithm programmed within said capnography device MCU, and c) synching all of said programmed capnography waveform generating algorithms within said pre-selected external locations for data reception, verification, and processing thereof to generate a continuous waveform at each of said locations in relation to said subject individual's respiratory status; wherein such verification provides block chain capability within said system for complete reliability of data. Basically, such an alarm code reflects specific results in relation to the measurement recorded within the generated capnography waveform itself, thus providing a different result for each waveform possibility (of which the number is myriad). The raw data from the sensor related to the carbon dioxide concentrations of a subject patient's exhalations thus will most likely never result in the same measurements twice, thus resulting in separate waveforms as generated within the different components of the system being identical or not. Identical results as to alarm codes indicate the system is functioning properly; anything else within regard to such comparative alarm codes within the different system device components show a problem exists that needs attention or the results will not be accepted. As well, such a system may operate wherein said data capture cycles are undertaken within a first set time frame and, upon generation of an alarm and notification of carbon dioxide level issues, said data capture cycle time frame is modified through a pre-set procedure within said capnography device MCU with notification thereof to said external connectivity base, said drug delivery device operating system, and said data center in order to continue verification protocols for all such captured data and transfer of data packets thereof transferred to said external locations. With such raw data driven operations, and the ability to utilize such mirrored (same) capnography waveform generating algorithms within each device component, such resultant verification activity within the data center (and possibly throughout the entirety of the system itself) includes a block chain result.

Alternatively, the system may utilize the same basic protocol but with the MCU programmed to continuously receive and analyze sensor information regarding the capnogram associated with the breathing profile (carbon dioxide partial pressure, as indicated with microvoltage variations within the IR sensor, as one example) to compare for specific parameters. To that end, then, the MCU will include an algorithm to generate a waveform in relation to the recorded voltage differentials provided by the IR sensor per the levels of continuously recorded carbon dioxide measurements. With an excess of carbon dioxide or a measurement below a threshold minimum, or above a threshold maximum, for that matter, and continuing for a set amount of time (since a brief outlying measurement may not be sufficient for such an alarm protocol), the MCU will alert proper individuals and/or entities if such measurements thus indicate a distinct breathing problem or other like event associated with carbon dioxide generation and expulsion during respiration. During such a monitoring operation, the IR sensor measurements are not only converted to a waveform for alarm purposes by the MCU, but such raw data is stored within the capnography device data storage chip in data packets generated within pre-set time intervals and pursuant to definitive amounts of data per cycle generating such individual data packets. As noted herein, such data packets are thus in relation to specific times at which each cycle begins (I1) as the IR source and sensor are activated, at which time the IR sensor data is transferred to the MCU (D1) as well as the amount of such data transferred during such a set time duration, and which the MCU (from its cache or like saved data base) transfers the data to said capnography device data storage chip and, in the case of device alarm parameters being exceeded, creation of an alarm code (A1). The type of alarm code identified in data (A1) indicates any changes that the mirrored algorithm held at the data center and the external connectivity base should initiate in relation to the overall system interval or powerup time (I1). Thus, while the MCU utilizes the same generated raw data as is stored for eventual transfer and handling by the data center through a data packet interpretation and waveform generation algorithm, the same algorithm (mirrored) present within the MCU and the external connectivity base itself generates a monitoring waveform for continuous monitoring purposes. In this manner, then, the monitoring capability of the MCU solely performs such an operation for that purpose and does not store the data or generated waveform. The MCU data packet handling and eventual transfer to the external connectivity base device base station and on to the data center provides a full capnogram waveform for a physician, etc., to then utilize for patient analysis, diagnosis, and treatment purposes thereafter any such notification occurs. The resultant data center waveform generation thus provides a data and time stamp and overall block chain result with regards to such data as the I1, D1, A1, and data packet size limits all provide integrity to the type and amount of such raw data for conversion at the data center level such that complete reliability is permitted and provided in relation thereto. Furthermore, the system itself actually functions within a UDP protocol at that point, with, however, a further capability of instead of moving forward with only data that is present and provided within and at a location for handling at the moment of transfer (as is customary within a UDP system; if some data is missing within such typical UDP protocols, the system moves on and does not require for further functioning all such data), the provision of the I1, D1, A1, and data size limitations accords the system the ability to have all such data correlated within the data center (and external connectivity base) for complete compilation thereof for, again, full data packet integrity for a true and reliable capnogram waveform generation for physician, etc., review, at least.

Thus, if at the MCU level, and during waveform generation by the algorithm present therein (the same algorithm that ultimately generates the waveform at the data center upon data transfer from the external connectivity base and then to the data center), a result of sufficient time resides outside the thresholds (minimum or maximum of carbon dioxide exhalation), and thus notification thereof thus occurs, the overall system then provides such stored (recorded) data within either the MCU or, for instance, a micro SD card (or like implement) present within the capnography device itself to the connectivity base, through RFID, inductive coupling through placement of the capnograph on a proper device on (or around, perhaps) the connectivity base itself. As noted above, this activity serves a dual purpose of such data transfer (for ultimate transfer to the data center of raw data for algorithm conversion to waveform through data packet block chain operation) and power up of the capnograph for further utilization thereafter. As well, the MCU will then, once the capnograph is returned to a proper monitoring location by the user, store and transfer subsequent sensor data within its cache for immediate transfer using the RFID tag for inductive coupling as noted above. In this manner, and dependent upon the availability at that moment for RFID transmission to the external connectivity base, whether such transferred data is provided through interrogation and response between such external connectivity base and RFID tag or, if necessary, and as alluded to above, as well, directly from said MCU to either said external connectivity base or said external data center through the wireless, Bluetooth, and/or cellular transmission capabilities. Either way, and as described below in greater detail, such data transfer is handled reliably and with integrity without processing until such data is properly considered in relation to the specific parameters of data capture and storage provided within the configuration of RFID tag, device data storage chip, MCU, etc., of the inventive capnography device. Additionally, the data from the sensor (and thus transferred initially to the MCU) may be further transferred not just to the base and/or data center, but also to receiving devices (such as, without limitation, smart phones, such as within at least one app, computers, and the like, basically any device accessible via the internet through wifi, Bluetooth, etc., communication protocols) associated with recipients authorized for such a purpose. Thus, without limitation, the individual's physician may have transferred to his or her computer device (again, smart phone, computer, etc.) such data in raw form for eventual compilation in a waveform for analysis and diagnosis, if necessary. Thus, as with the MCU, the base, and the data center, such a recipient device will include the same mirrored algorithm for such compilation purposes. Importantly, however, the algorithm in all such locations and devices is utilized primarily as a means to verify the transferred data in raw form prior to actual compilation and thus processing. As noted above, each data packet generated through the parameters of each data cycle includes an I1 value associated with the exact moment such a cycle begins, the value (D1) associated with the transfer initiation of data from the sensor to the MCU until the MCU powers down the device (which thus creates the cycle upon which the MCU powers up the device as I1 and the new cycle begins with data transfer from IR sensor to MCU as D1) at which time such data transfer ends, and the actual size of the data transferred during such a cycle (which is considered a static amount in relation to such a time elapse and part of the D1 value). Also present is an alarm time (A1) that is provided by the MCU once the alarm is undertaken and an alarm code is generated by the MCU algorithm that ultimately modifies the data generation and capture of the device thereafter to determine and verify the reason for such alarm generation. The alarm code generation thus causes the algorithm (and thus MCU) to stream all further captured raw data to an external location including the same (mirror) algorithm, including, without limitation, and depending on pre-selected and authorized subject recipients, the base station, the data center, and any other computerized device that may receive such data via wi-fi, Bluetooth, and/or cellular communication protocol directly from said capnography device associated with said patient/individual. Thus, each algorithm location will receive the same data packets as they are generated (subsequent to an alarm, of course, which first indicates there was an excess or lack of sufficient carbon dioxide within the patient or, again, other individual) exhalation measurements. As these data packets are received, each value for each cycle is sought in order to permit compilation thereof as the total amount and proper I1, D1, A1, transferred data size, and final time must meet specific expected targets. If such targets are not properly filled, the data is not verified for further processing, thereby allowing for the overall system to check one device result with another for complete verification of data integrity before any data processing is undertaken, thus allow for prevention of any hacked material, and, perhaps more importantly, provision of data that will result in a complete and true waveform for patient/individual health and security. Such a data integrity protocol within the overall capnography system provides a reliable blockchain program, as well, since the data involved must be verified within all algorithm-containing devices before any processing is permitted. The specified data size requirement effectively prevents any inclusion of unexpected (hacked) data or other information introduced therein. In such a manner, no hacking is allowed as the different devices within the overall system will not process any raw data until such verification steps are completed. In this manner, then, the overall system allows for a single IR sensor to be monitored, ultimately, by any selected number of external devices as well as the capnography device on which it is present, with the ability of the synched mirror algorithm within such external device to verify the raw data transferred thereto from said capnography device as well as provide continued individual respiratory status and capnography device status simultaneously through systems checks associated with such received raw data. The overall system thus provides a unique benefit that a capnography device may be remotely controlled and monitored with automated systems checks to permit utilization at any location with continued monitoring and surveillance. Additionally, if the algorithm does not function properly in association with the MCU of the device for some reason, the MCU may then, without an initial alarm as to carbon dioxide concentration measurements, and as another system check capability, stream the captured raw data from the IR sensor directly to any or all remote mirrored algorithm locations in order to provide constant monitoring and surveillance of the subject individual's respiration status by such remote devices (base station, data center, authorized individual recipients, etc.) with alarm code and notification supplied in such a manner, if necessary.

As it concerns, then, capnography, such a system may include a capnography device and/or method utilizing the same, as described generally below:

a capnography device comprising a three-dimensional housing, said housing including:
a) a hollow pass-through chamber,
b) at least one MCU including an internal clock and an algorithm for translating raw data to a capnogram waveform,
c) at least one IR source,
d) at least one IR sensor,
e) a component to provide secure identification of said subject patient in relation to said system components, said component being either i) a RFID tag (ISO/IEC 18000-7:2014 interoperability standard) to transfer such data to an external RFID reader imbedded in connectivity base, or ii) a NFC tag and antennae to transfer such data to an external NFC reader (said NFC tag being compliant with and utilizing the ISO/IEC 15693 standard, as one possibility);
f) one or more communication devices for direct communication with said external connectivity base (or possibly said external data center), said devices selected from the group consisting of wireless (wi-fi), Bluetooth, cellular, and any combinations thereof;
g) a separate data storage device associated with an inductive coupling component; and
h) at least one power supply associated with said inductive coupling component;
wherein said IR source and IR sensor are configured on opposing sides of said pass-through chamber and aligned for emission of an IR beam directly towards said IR sensor;
wherein said IR source is programmed to emit an IR beam within a range of from 4.26-4.30 micrometer frequency;
wherein said microprocessor unit is connected to said IR sensor to permit transmission of data from said IR sensor to said microprocessor unit;
wherein said microprocessor unit includes a flash memory component that is formatted to receive said IR sensor-transmitted data;
wherein said microprocessor unit includes a program to format said IR-sensor transmitted data for proper transmission to produce proper capnography waveform to and write on capability on said RFID tag or said NFC tag, and said device data storage chip;
wherein said power supply continuously provides electrical power to said IR source, said IR sensor, and said MCU;
activates said IR source and said IR sensor upon activation through said MCU, or, permit transmission of power from said power supply to said IR source and said IR sensor;
wherein said IR sensor generates data from the emission beam passing through said open chamber from said IR source;
wherein said data generated by said IR sensor automatically transmits to said MCU;
wherein said MCU performs a regimen of activating and deactivating said IR sensor and said IR source at a set time interval in relation to said MCU internal clock, thereby limiting the actual amount of data transmitted by and received from said IR sensor within each activation/deactivation cycle in order to thereafter and therein permit said MCU to store all transferred information from said IR sensor within its flash memory;
wherein said MCU is programmed to stop receipt of information from said IR sensor and power down both said IR source and said IR sensor in evenly timed intervals, whereupon said MCU transfers said information to data storage chip;

wherein said MCU is simultaneously and separately programmed to receive said data and generate a waveform therefrom through utilization of said algorithm, thereby allowing for continuous comparison with specified parameters of low and high thresholds of carbon dioxide levels for pre-set time intervals within said waveform associated with said sensor results, wherein if such results fall outside said parameters, said MCU alerts proper individuals and/or entities of such an occurrence;

wherein said MCU automatically formats and transfers all received and stored information to said device data storage chip as data packets for eventual transfer to said connectivity base and then to said data center wherein the same algorithm present within said MCU is utilized to generate a waveform for archival and medical provider viewing purposes, said transfer provided through inductive coupling operation at the connectivity base via contact with said capnograph;

wherein said RFID or NFC tag sends all received information form said MCU to said external connectivity base upon each interrogation and/or inductive coupling, or, if such a communication route is not possible (for instance, the reader is outside the range of communication with said RFID tag), then the wireless, Bluetooth, or cellular communication device is utilized for such a purpose;

wherein said suitable external connectivity base transfers all received information from said at least one RFID or NFC tag and/or wireless, Bluetooth, or cellular to said data center;

wherein said separate storage device is programmed to receive information transferred from said MCU and subsequently transfer said information to said external connectivity base through said inductive coupling component, of which said external connectivity base includes a complementary component such that contact therebetween allows for such information transfer;

wherein said at least one power supply is replenishable through said inductive coupling component and whereupon such contact therebetween said inductive coupling component and said complementary component included within said external connectivity base device base station allows for charging of said at least power supply; and wherein the total size of said housing, within which all of said components are attached and present, is defined by a range of 3 to 10 centimeters wide, a range of 3 to 10 centimeters long, and from 3 to 10 centimeters deep.

As it pertains to the potentially preferred embodiment of utilizing a miniaturized smart sensor capnography chip device as the initial sensor, such may be embedded into and/or within a capture chamber ring. Such a ring preferably is sized to attach to the standard end of an endotracheal tube and/or tracheostomy tube (since all these ventilation appliances have standard diameter). Such a capnography smart sensor chip includes low energy IR source (such as, without limitation, a filament of a quartz tungsten halogen lamp engraved into a silicon chip) with a focusing lens narrow band IR filter for 4.26 micrometer wavelength (based on the Abbe number of the glass) with an opposing IR sensitive material (PbS, PbSe, InSb, or CdS) fused into silica with a thin sapphire coating shield for filtering, again, as non-limiting materials. A slight curvature in the microchip along with the aforementioned focusing lens allows for the IR beam to be directed toward the IR sensitive material embedded within the chip just under a thin layer of sapphire. The $CO_2$ from the patient/individual will disperse equally throughout the chamber ring to provide a small sampling area in the middle thereof to derive a suitable overall $CO_2$ concentration as well as to then detect the changes in such a concentration based upon the target patient/individual's respiration levels causing the displacement of the $CO_2$ sample in the chamber.

The capnography (miniaturized) smart sensor chip is less than a millimeter in scale, at most 1 and preferably around from 0.01 to 0.5 mm, in length, width, and depth. Such a chip should be programmed to cycle the IR source to acquire the most efficient HZ required to generate an appropriate capnography waveform. The sensor should also have the programming to adjust cycles in relation to temperature and pressure and a memory cache to hold at least 30 min of raw data acquisition.

The smart sensor capnography chip is provided with such a ring chamber that fits easily within and is held appropriately (tightly, snugly, etc.) as needed to reside within a base housing component but may be easily removed, if needed, without damaging the housing, chamber ring, or chip, itself. Such a housing will thus be configured to allow for such introduction of the chamber ring/chip component (such as a proper snap-in action with proper alignment therein) and further includes a base material that allows for sufficient retention thereof the chip and chamber ring, particularly if the chip is curved in relation to the lens portion thereof for directional capability between the IR source and IR sensor components. The base housing thus also includes the other components necessary for utilization of the remote surveillance and notification capabilities thereof, as well as communication capabilities with a base, data center, and/or other devices authorized to receive such notifications upon an alarm result in relation to the patient/individual respiration status. Thus, included are the MCU (including the mirrored algorithm present within such other communication devices and locations), the power assembly to operate and actuate the IR source as needed (with the MCU including programming to control such actions), the RFID tag for communication with the external base as well as facilitate the charging of the device via inductive coupling, and the communication (connectivity) component for data center and/or other device transmissions, thus including Bluetooth, Wi-Fi, and cellular antennas, etc., for such a purpose. The power assembly (source) is rechargeable in any type of suitable manner (battery, graphene, etc.) and must keep such power for IR source operation (at least) for a minimum of 26 hours with a minimum of 4 hours of data streaming as well. Additionally, the housing includes a data storage chip therein that receives raw data from the smart sensor chip in relation to the target patient/individual's respiration status (as discussed above) for access by the MCU component for determinations of respiration status for alarm monitoring and surveillance. Such a data chip may be of any typical construction and make for such a purpose, and must also retain at least 26 hours of continuously streamed raw data from the smart sensor capnography chip. The MCU in the Housing should be able to take the raw sensor data transferred from the capnography sensor chip and create a suitable capnography waveform. All alarm parameter programming is also retained within the housing MCU which also directs the initiation of data transfer via one of the data transfer methods (Bluetooth, Wi-Fi, cellular, etc.). Additionally, the MCU also transmits the raw data to data storage chip which must hold, as noted above, at least 26 hours of raw sensor data. The housing MCU also verifies the proper functioning of the sensor chip (such as the receipt of data for raw data conversion to capnography waveform initially for alarm purposes; if the I1, A1, D1, and/or data amount values do not meet expected values, then, as noted above, the system may determine a problem exists within the smart sensor capnography chip). The housing MCU alarm limits must be adjustable to the target patient/individual in terms of acceptable $CO_2$ levels in relation to time as well, thus allowing for programming of the MCU for such a purpose. In addition, there should be alarm parameters in relation to respiratory rate for the target patient/individual which is derived from a suitable capnography waveform.

As discussed above, an external base station is utilized in conjunction with this smart capnography sensor chip/housing device that provides the charging of the housing power source through inductive coupling. Additionally, this inductive coupling capability allows for raw data transmission (if the alarm system is activated, as noted above) and should provide 7 days of raw data storage and contain a mirrored algorithm or exact duplicate of the algorithm held in the housing MCU. The base station should also provide connectivity for up to 7 separate housings or devices. The external base should provide internet connectivity and or LAN connectivity.

The external data center, again, as noted above, will also include a component with the exact mirrored algorithm present within both the housing MCU and the external base station. This will provide mobile access for healthcare providers and/or other monitors to view the target patient/individual's capnography waveform for diagnostic purposes.

Overall, then the inventive method may potentially be interpreted as: a method of providing continuous surveillance and external notifications for a target patient in relation to his or her respiratory status and condition, said method including the steps of:

i) providing said capnograph of above;
ii) providing an external connectivity base device base station attuned for transmission of signals to and receipt of data from RFID tag, NFC tag, Bluetooth, wireless, wifi lan, and/or cellular;
iii) providing a data center external to both said external connectivity base and said capnograph, said data center attuned with said external connectivity base to receive data transmitted from said data RFID tag, NFC tag, wireless, Bluetooth, or cellular, and/or wifi thereto, and said external data center including at least one mirrored algorithm and/or rules engine to analyze and act upon said received data;
iv) introducing said capnograph within an oxygen delivery device or as a standalone device, wherein said capnograph is placed in close proximity to said target patient's mouth and/or nose to allow for exhalation samples to pass through said chamber;
v) having said MCU power up said IR source and said IR sensor;
vi) receiving said exhalation samples within said capnograph chamber wherein said activated IR source provides said IR beam from one side of said chamber to said activated IR sensor on the opposing side of said chamber, wherein said IR beam, when powered to emit, excites molecules within said chamber present samples at that moment in time to permit measurement of concentration of carbon dioxide during each power up status in relation to fluctuations of voltage measured thereby;
vii) transferring said captured measurement data from said activated IR sensor to said MCU unit, said transmission of data causing said at least one MCU to receive said data and, through an algorithm, generate a waveform from said data to compare continuously with set parameters of high and low thresholds for a target patient, wherein if said carbon dioxide concentration measurement falls below or exceeds such thresholds, then said MCU immediately alerts said patient and any other pre-set persons and/or entities of such an occurrence, and the also subsequently indicates deactivation by said MCU, thereby causing said IR source and said IR sensor to power down until reactivated by said MCU, wherein said MCU unit remains activated for receipt of data, but is limited to such data transmitted by said activated IR sensor, wherein said post-alert transmitted data is stored within said flash memory of said MCU and all data prior to such an alert is transferred to a separate storage device (micro SD card, for instance);
viii) formatting of said post-alert transmitted data stored within said flash memory to a suitable language and/or format for transmission via Bluetooth, wifi lan, cellular and transmission and writing alarm code on said RFID or NFC tag; and
ix) repeating each step indefinitely thereafter in cycles;
  wherein said external connectivity base received data is transmitted to said external data center in relation to the identity of the target patient associated with said capnograph and said external connectivity base, wherein said external data center may receive such stored pre-alert data and all post-alert data is provided for continuous comparative review of said target patient's standard breathing for further surveillance purposes, wherein any deterioration and/or degradation of such a waveform signal will further allow for target patient physician, notification, emergency notification, or both, dependent upon the severity of any detected deterioration and/or degradation.

The programmed MCU provides for cyclic type powering up and down of said system, there is, for capnography purposes, an IR source and a juxtaposed IR sensor as well as a battery for providing sufficient power to such a source (other types of sensors may not require such power levels, but, such an IR system actually requires lower amounts of power than those that remain in an activated state indefinitely).

Thus, in relation to such a device the MCU, acts as a system initiator. The MCU remains dormant for data acquisition until it receives data from the sensor which requires activation of the system by the MCU. The MCU internal clock is set for a cycle requirement (such as for instance, and without limitation, a 10 hertz cycle, or 100 microseconds) which is the processing time. The MCU clock starts with a "wake up" secondary to receiving data from IR sensor and receives data from the sensor for the cycle time amount (for example, without limitation, again, 100 microseconds, or a 10 hertz cycle) based on the internal clock setting. Subsequently, the MCU programmed process is initiated at the end of each (10 hertz) cycle, at which time the MCU deactivates the system deactivating the sensor source and sensor. Thereafter, and the second process of the MCU, it transitions sensor-received data held in flash memory therein into proper format to produce a proper capnography waveform for evaluation purposes including potential alarm activation. Then the MCU sends the raw non-process data to the data storage chip. The MCU clears its flash memory cache and "sleeps" until said internal clock with algorithm causes the MCU to initiate system power-up and to monitor for the receipt of data from said IR sensor. As noted above, for process checking purposes, the MCU should be connected to the system in a manner which allows MCU internal clock with algorithm to provide system power-up. Also, the CPC codes for the RFID tags are also used for patient/device/item identification utilizing a tokenization method for security purposes (if needed). The external connectivity base ID is thus used to assign other information for identification purposes (such as facility and doctor identifications for health patients, for one non-limiting example). The RFID tag CPC codes and external connectivity base ID codes are used together to route information and data sent from connectivity base to data center for routing to an appropriate mirrored algorithm and or rules engine/machine learning AI within the database, as well. The MCU acts as the power regulator, but acts similarly otherwise to receive data from the IR sensor and transfer data to the device data storage chip.

Such a system, however, potentially preferably utilizes the MCU as an initial gatekeeper to determine threshold capnogram measured results (in an algorithm-generated waveform) from a target patient to determine if such a person necessitates medical aid due to exhalation (respiratory) levels falling outside parameters over a set time interval for acceptable and/or normal considerations. Thus, although, as above, the MCU can cause the cyclical capabilities of a capnography system to monitor, capture, and send all data continuously (in cycles) to a connectivity base and ultimately a data center for data processing, the system, again, potentially preferably, functions to provide any alerts as to respiratory problems (in terms of exhalation measurements for carbon dioxide) primarily. In such a situation, the MCU not only receives all such continuously generated results, but creates a capnoform (waveform) separately from such data that allows for the comparison capabilities for notification purposes, as noted above. Such an operation is configured for 24-hour intervals overall to such monitoring purposes before power supply replenishment, and thus inductive coupling activation for such a purpose, with the simultaneous transfer of stored raw data (the same data utilized by the MCU algorithm to generate the monitoring waveform) to the external connectivity base and then to the mirrored algorithm in the data center for compilation and ultimate archival waveform generation. Thus, upon inductive coupling activation to such an extent, the user then places the capnograph back to the desired location near his or her exhale stream for further operations to such an extent. As noted previously, then, if at any time the threshold measurements are outside the acceptable parameters for a set time interval in relation to the waveform generated by the MCU algorithm, the MCU provides a protocol for immediate notification to the target patient, medical provider(s), and/or emergency personnel. Additionally, then, the storage to the separate storage device ends and then the MCU undertakes the cyclical capabilities noted above to eventually write alarm code to the RFID tag and then such data is transferred, whether by interrogation and response by said RFID tag, through wi-fi, Bluetooth, and/or cellular channels, to the external connectivity base (dependent on which communication capability is available and/or most effective and/or efficient at that moment in time), which then transfers the same to the data center.

With such an overall system and capnograph device, the user has what may be termed as a passive notification protocol to best ensure complete monitoring and notification of breathing status is provided. In this manner, then, the user is supplied not only with a device that permits complete monitoring of his or her breathing status, but such also provides a system that alerts if, for instance, the user falls down, passes out, or otherwise has lost any capability of actively requesting help or medical attention. To further such an overarching capability, the capnograph may further be supplied with an accelerometer component to indicate if and/or when such a device is, for instance, dropped, atypically moves in one direction, or otherwise acts or is activated in a manner than is not conducive to standard wearing and utilization. In other words, the inclusion of such an accelerometer accords a more complete remote presentation of the status of the device, and thus status of the user, for that matter, in that the potential for loss of sensor data (or at least data recorded within set parameters associated with proper capnograph placement on or around the user's respiratory exhalation stream) may be accounted for if such an accelerometer records an activity simultaneously with any skewed or insufficient data recordation. In this manner, again, a more robust and/or complete explanation of the overall patient/user breathing status is provided with the continuous monitoring through the MCU-contained (and/or external connectivity base and/or external data center) algorithm and IR sensor measurements.

The overall system further includes some assumptions and standards for operational guidelines and purposes. It is important that the MCU acquires a set amount of data packet samples (100 microseconds/10 hertz of data, for example) to allow for the exactness of time and data size (possibly) for the database to match data requirement in mirrored algorithm in relation to such specifics. The number of cycles per minute may be attenuated as needed throughout the system through the programming of device MCU algorithm and mirrored external connectivity base and/or external data center algorithm. The RFID tag CPC code is used by the system and not in any way by the customer. An RFID tag number is the CPC code and cannot be read by the human eye in any manner. The system may be supplemented by a login and password for the patient/device/item portal and may further employ (simple) out of band verification for safety in this manner, if necessary. Such out of band protocols may use open source OATHE protocols, and additionally, or in substitution thereof, it may utilize an EMOJI device (such as driven by systems developed by Symshield).

Such a capnography device may be provided in a miniaturized size and state in comparison with typical capnography instruments. Such may simply snap on/clip to an established structure (such as a CPAP mask, nasal cannula oxygen delivery device, and the like) with the components as presented within the drawing and described above. Additionally, such a device may be implemented with any type of structure that allows for close proximity to the mouth and/or nose of a subject patient (or monitored user, if monitoring is desired due to physical situation and/or status, such as, as non-limiting examples, a truck driver, a pilot, a mountain climber, a SCUBA diver, a long-distance runner or biker, and the like); thus, again, as one example, a microphone attached to headphones may include a snapped in device as described and disclosed herein to monitor such breathing conditions. In any event, such a capnograph fits on a patient's face with nasal prongs pointed upward and in a side slot end piece; its size is about 1.2 cm cubed is placed into each side with a cable coming from each cube. Such a small size device, coupled with the remote monitoring discussed herein with an external connectivity base and storage database accessible by such an external connectivity base under any standard wireless communication protocol, permits a number of beneficial results for a patient. Different options are mainly in the form of multi-system integrated monitoring such as perimeters for wandering patients, healthy lifestyle optimization such as having monthly report read by a physician, and they can order the small component pieces of such a device easily for repair, etc., more often. Again, with IR sensors, at least, a certain amount of continuous battery power is needed to account for the high requirements of such a sensor and source. Thus, a graphene, lithium ion, or like, battery (compact for the small device) may be utilized having a battery life for the capnography device of roughly 24 hours possibly more through MCU programming in relation to patient condition and alarm status for system power up. The recharging procedure occurs through inductive coupling using the reader device base station, and additionally a micro-USB plug may be placed on the device, if necessary. It may have a USB connection so it could charge using all the options available to cell phones or other devices including wall plug, computer, or those small devices which provide remote charging capabilities. Charging may also be accomplished while the device is actually worn, as well. The system would include a low battery alert which can be send to cell phone, call landline using VOIP and we could add an indicator light to device (very small LED).

Alternatively, the system may include an NFC component for MCU transfer and reader transmission, if desired. Such NFC components provides the mobility with the tap and pair functionality out of the box. The patient/device/item provides a wifi or LAN ID and password so that the external connectivity base may work and link in as soon as it comes out of the box. The patient/device/item can then access the appropriate communication portal for the ability to change external connectivity base settings remotely. Since the system does complete device functionality checks continuously, if for some reason such requests are missed, such can be handled remotely by a suitable technical team as any missing external connectivity base data calls would require intervention to ensure the device is functioning properly. In addition, if needed, the patient/device/item would be notified to switch to NFC and cellular protocols until the system is corrected as needed. Additionally, there can be provided an app or like program for download to a communication device (smart phone, for instance) which provides parameters that can be updated so that the device only sends to the data center at the moment of wifi link, LAN link, or if data coming from the device falls outside of set parameters. Such travel, mobility, and hardware factors are important components of the system versatility, as well.

Thus, in terms of the potentially preferred embodiment relating to capnography, such an inventive system relates to a capnograph including a suitable sensor to monitor (and measure) carbon dioxide concentration and respiratory rate for a target patient. Such a device utilizes a RFID or NFC component for recordation of alarms and Bluetooth, wifi, or cellular, and or inductive coupling transfer of capnographic information from the device to an external connectivity base and ultimately on to a data center for constant monitoring and immediate notification as needed. Such information is gathered through a repetitive infrared (4.3 micrometer wavelength) source and appropriate sensor that cycle in terms of power up and down in relation to MCU algorithm programming. The IR source and sensor are oppositely configured on sides of a breathing tunnel component within the device to permit continuous and cyclical excitation of present carbon dioxide ostensibly to create an initial reading for the target patient's capnogram in relation to voltage differences over time. The IR sensor is connected to and transfers collected data to a microprocessing (MCU) unit that stores such information within its flash memory, shuts off the overall system power, formats the received and stored data, and transfers the formatted data to the capnography algorithm for interpretation and possible alarm activation. The programming in MCU provides cyclical powering of system. The MCU triggers power down of the IR source and sensor (to prevent burnout and allow for cyclical measurements) until the data acquisition time limit is reached as defined by MCU programming. sending data to the device data storage chip, and so on. Such causes immediate transfer of all data transferred from the MCU to the device data storage chip, to transfer to the external connectivity base and on to the data center. At the data center, the received data is transitioned from such raw data into a capnographic waveform through the utilization of a mirrored algorithm and/or rules engine. In this manner, a base waveform is developed for each target patient and the repetitive readings create a means to create a standard by which all further monitored breathing ($CO_2$ measurement and respiratory rate) for such a target patient is compared. Any degree of deterioration from the standardized measure is analyzed for the potential for intervention with assessments for routine physician notification up to emergency notification, all provided through the encompassed system itself. Thus, the capnograph device essentially provides the means for constant, real-time, and remote monitoring of a target patient's $CO_2$ inhalation and exhalation concentration data, respiratory rate, and consequent overall respiratory status with fully reliable identification of the patient, location, and treating physician, as well as automatic notification to all necessary parties should a compromised measurement exist at any time the device is properly worn and utilized. Such a device allows for a number of beneficial results, improving the monitoring and treatment of patients having respiratory conditions, at least.

Patients, care givers, and medical providers can be notified immediately when the capnography reading (through the capnography waveform generation via the algorithm within the capnography device as well as all the other required system devices) falls outside of individual patient directed parameters. In addition, the system provides a mechanism for sample acquisition interval adjustment in real time based upon need. This provides both the benefit of energy savings and the ability to increase level of monitoring as needed. This need may be identified by one or multiple reading outside of defined patient profile monitoring parameters or by the identification of trends noted in the patient predictability modeling of patient health status decompensation. This gives the patient's healthcare provider with a more complete and detailed report highlighting the need for possible intervention that patient has shown with previous health status change. The sample acquisition interval is controlled by the increase in the Hertz cycle of the MCU which is in direct relation to the static MCU internal processing clock. Additionally, as alluded to above, the health care supplier (physician, nurse, etc.) and/or monitor may receive such raw data concerning the patient/individual through direct communication from the capnography MCU to their own device where the same algorithm as within the capnography MCU, the base, and the data center is present to provide the necessary verification of each data packet supplied thereto allowing for generation of the subject patient/individual's capnographic waveform for continuous streaming subsequent to an alarm code generation to permit monitoring thereof and, if needed, diagnosis and/or determination if medical attention is required and at what time. As also alluded to above, this overarching system thus allows for complete verification of data in every instance it is transferred prior to any processing thereof, from patient to provider and elsewhere, as needed. Coupled with the alarm capabilities discussed above, the overall system thus provides a complete and continuous surveillance and notification program for any and all individuals present in a situation where external exhalation measurements are of significance. Thus, the capnography device may be included within typical oxygen, etc., tubes, clipped thereon or provided as an add-on structure to capture exhaled breaths. Thus, the range of utilization of such a system and capnography device is extremely broad from typical injured persons within a hospital setting (such as a patient treated with certain high-powered anesthetic, to intensive care monitoring; including, without limitation, neonates), to CPAP users, to crib-based infants to monitor breathing, to airline pilots, to scuba divers, to semi truck drivers, basically any situation that allows for wireless monitoring and possible alarming of respiration concerns, may be included within such end-uses.

Patient healthcare providers (or analogous device manufacturers/suppliers/repairpersons, etc.) will be able to request a standard capnography (or other sensor device reading, etc.) report for reading in addition to the notification in change in patient capnography data which may include falling outside the defined parameters for patient profile for acceptable $CO_2$ level or by system identifying trend noted in patient predictability model with the data associated with system prediction sent to a healthcare provider and or patient. The health care (or other type) provider can have secure individual configurable API access with multiple options for notification, report views, sorting, etc. In addition, medical (or like) facilities or other groups or individuals which are identified by patient as needing access to respiratory status capnography monitoring may also have a filtered view secure individual configurable API based upon need and patient or healthcare provider direction.

The patient profile may also be configured to used data from other systems such as bed alarms, perimeter alarms, or other systems to configure a secondary or dependent rules engine to enhance functionality for those such as dementia patients in relation to wondering or getting lost using the systems indicated above. In addition, the system can send other respiratory systems such as CPAP, Ventilator, or other oxygen delivery systems real time data regarding respiratory status for titration, or modification of therapy parameters such as increasing $FIO_2$.

The capnography device may also be utilized within monitoring systems and devices, including, without limitation, gas masks (such as to provide protection from smoke, chemical reagents, and/or other toxic/dangerous substances, ostensibly to allow for the user/wearer's respiratory condition to be monitored from any location during utilization), particulate masks, scuba systems, airplane pilot oxygen monitors (whether passenger, delivery, fighter, etc., jet pilots), anesthetized patient monitors, and any other type of device for respiratory monitoring purposes.

Viewing this as an analogous system in relation to anything having a continuous monitoring capability and the need for raw data capture, but processing only after any determination (definitively) of the presence of unexpected data within a transferred data packet, it should be evident that any type of measured consideration for condition and status surveillance (and possible notification of difficulties therein) may be implemented in the same basic fashion, particularly if remote utilization and requisite device monitoring, in addition to patient/individual status, provides such beneficial results. Thus, the overall inventive system and method is not to be taken in any limited manner or fashion with this disclosure and all due breadth and scope should be accorded in relation to the actualities provided herein.

Of potential interest is the analogous nature of utilizing such a system with a telematics component as the drug delivery component. In such a manner, for instance, within a semi-truck environment, for example, a telematics component is utilized already for certain control elements (slowing a truck when followed by a police officer, for instance), keeping track of paths and movements (through a GPS feed and contact), and other concerns. The substitution of a telematics component for the drug delivery type here could allow for a user (driver) to utilize a capnography device that monitors for time driving, actual wearing of a needed breathing mask (CPAP, for instance) while driving or at rest, and even the driver's actual breathing status (to monitor for potential exhaustion or sleepiness, as examples). The generation of a waveform by the capnography device may indicate any of the above situations, with the potential to actually monitor conditions of such a subject driver wherein the generation of a waveform outside of parameters for such a person may generate an alarm and send raw data thereafter to an external base (such as an inductive coupling device that may be plugged into an electrical socket; as above, such a base may be utilized for charging alone or for data transfer while charging through the Bluetooth, wireless, etc., communication components), a data center (dispatcher, for instance), and the telematics system. As above, such components would include the same capnography generating waveform algorithm in order to separately create waveforms that then associate (or not) with the generated capnography device alarm code. If all such device components first decrypt the raw data properly and then match alarm codes, then the system allows for continued raw data streaming and waveform generation with the telematics component monitoring for any necessary activity (reporting, overtaking driving operations, slowing down, etc.) in relation to a parameter pre-determined for such a response for the subject driver. The capnography device may also be outfitted with an accelerometer or like component to monitor for the user's posture status (particularly while driving). Any significantly long period of showing such a driver has leaned too far in one direction, for instance, may create a need for alarm generation or even dispatcher communication. Such a system of course, may be utilized for all types of drivers (car, bus, train, motorcycle, plane, and the like) for such safety and health purposes. In any event, such an overall capability may be employed in relation to any separate device in this manner within such a system for capnography related monitoring and responses.

Furthermore, of particularly important benefit it is noted that since the initial device only generates, captures, and transmits only raw data, such an overall system provides a mechanism for multi-party dynamic encryption without increasing data packet size caused by encrypting the data itself through other standard encryption methodologies. Thus, since the captured and transmitted amount of raw data from the IR sensor/smart sensor chip to the MCU of the device is limited to an exact value, the data packet sizes cannot be altered without causing the system to refuse such raw data, thereby, again, providing a multi-party dynamic encryption capability for reliable data capture and utilization.

No limitation is intended with this disclosure as to the utility and breadth of the overall system of providing data integrity described herein, including, without limitation, the myriad end uses and industries such may be provided to and for and utilized within, the block-chain capabilities such a system provides within any such industry alluded to above, the artificial intelligence capabilities such a reliable data capture and transfer method provides within any industry, and any device and/or method implementing and/or employing such a disclosure provided herein.

Additionally, such an invention may further encompass the utilization of a unique combination of such device components with external conduits, gate keepers, filters, and algorithms. Thus, also encompassed herein is a method of providing continuous surveillance and external notifications at a data center location for a target patient in relation to his or her respiratory status and condition through a cycled process including the utilization of a capnograph as defined above, wherein said external data center includes i) an algorithm mirrored in relation to algorithm imbedded into device MCU to provide the exact results in relation to processed data in both device, external connectivity base, and external data center ii) a) to govern the functions of said capnograph, waveform generation including changes in sample acquisition interval as indicated by alarm code b) to act as a gatekeeper for data receipt, and c) to provide modifications to the frequency of cyclical data capture and generation, iii) an algorithm for processing data from data packets to create an exact capnography waveform to be used by medical provider for patient status evaluation, and iv) an algorithm for processing data from said external connectivity base and or device including but not limited to an exact algorithm mirrored to precisely match algorithm held in device MCU and said external connectivity base.

As further alluded to above, the system allows for the incorporation of at least one drug delivery device in order to provide automated drug delivery operations in response to subject patient capnography waveform results. In such a manner, the entirety of the capnography and drug delivery devices of the overall system may be provided as individualized, even worn, structures allowing for continuous and portable monitoring and drug delivery capability, thus permitting such a subject patient the ability to move around, travel, and any other mobility need or desire without compromising or sacrificing effective monitoring and treatment in relation to a capnography-based condition. Heretofore, the only possible means of relating the two types of monitors and delivery devices relegated patients to remaining in specific locations with IV towers, ventilation tanks, and the like, provided with large-sized capnography instruments, as well. Additionally, the prior possible procedures of coupled capnography and drug delivery devices did not take into effect any internal checks as to instrument/device operation, let alone required continuous power-up limiting the ability to undertake such processes without requiring outlets and plugs to ensure long-term activation and utilization. In other words, the ability of the presently disclosed capnography/drug delivery system accords the user with an overarching system that allows for freedom of movement, low-power requirements (due to the intermittent generation of waveform results from the IR sensor measurements, and further transfer of raw data to the other system components if an alarm code is realized in relation to capnography measurements outside parameters for the subject patient, or through time interval-based raw data bursts to the other system components for short durations), automatic external connectivity base and data center communication of subject patient capnography issues or capnography device malfunctioning problems (thereby allowing for in-time notifications to the subject patient and any other pre-selected entity or entities as needed to ensure immediate attention is undertaken), and automated drug delivery operation modifications in response to any problematic capnography waveform results, all through the utilization of an error-proof mirrored algorithm base utilization and hack-free software (block chain) capabilities. Such an algorithm (the capnography waveform generating algorithm, as discussed throughout) is present within each system device, receiving raw data from the capnography device, not processed results, in order to separately and independently generate waveforms therefrom to provide the necessary checks between raw data as transferred initially and received at each system component. Any glitch or anomaly within the results, as checked between all generated waveforms as they separately generate an alarm code that must match all others completely to ensure the system itself is properly combined with the same encryption keys, for instance, for raw data receipt and processing at and by each component algorithm, indicates any problem within the system, the location of the problem, and the needed notification to ensure correction of such a problem is handled immediately. Again, such a system has heretofore been lacking within the healthcare industry.

This mirrored algorithm method thus allows the waveform seen on any and all devices in which a copy has been licensed with secure access. The RFID tag, in particular, includes an encryption key that may be utilized as a licensing basis. Without the specific tag that associates with all of the different system components (having the same capnography waveform generating algorithm, of course). The raw data received by the capnography device cannot be accessed upon transfer to the other devices, for instance. Such an encryption key can change, flip, and synch the encryption keys of the different system devices, as well, to continuously update the protections associated with such an activity. In this manner, then, control of the overall system is permitted through such an encryption key. If a problem is reported, for example, the data center may discontinue such utilization, thus rendering all actions effectively useless. The same may occur if a subscriber, for instance, fails to pay; the system may be easily shut down through such key deactivation. The RFID tag may further include a token that passes through both sides of the system to allow for further control and protection from outside interference and/or potential corruption.

The system functions through the initial operation of the IR sensor for carbon dioxide concentration monitoring (and measuring) with the occurrence of a recorded measurement outside parameters for a subject patient for a pre-determined period of time indicating a significant enough concern to generate an alarm code in relation to the recorded capnography waveform generated by the capnography device algorithm at that moment. The capnography device then transmits the raw data associated with the alarm code waveform to the other component devices (the drug delivery operating system, the external connectivity base processor, and, if utilized, the data center processing unit). Each capnography waveform generating algorithm at such device locations then process, if properly decrypted, the encrypted raw data from the capnography device itself and generates, separately a capnography waveform therefrom. If any resultant waveforms do not generate an alarm code, the system determines there is a corrupt component or compromised data therein. If alarm codes are generated, but any one of them does not match the others, then the same basic results is noted (corruption or compromise as to device and/or data). If all alarm codes match, however, then the system is accepted as viable and proper and the capnography device continues to transmit raw data for further capnography waveform generation at each component device, with the drug delivery device separately determining if need for modification of drug delivery is necessary for treatment of the subject patient. Such waveform generation and, if needed, drug delivery modification, is undertaken until the generated waveform no longer generates an alarm code from the sensor raw data as continuously streamed subsequent to initial alarm code generation by the capnography device. As noted above, random and constantly changing encryption keys which synch to the RFID tag key number in the base device, accord the needed capabilities to accept and process the raw data from the sensor at each capnography waveform generating algorithm within the overall system. Again, if any of the processors within such component devices fails to decrypt the raw data, then either the device issue is corrupt or the raw data as received has been compromised. The alarm codes generated in response to waveforms associated with such accepted (and thus decrypted) raw data are then, as noted above, utilized to determine the status of the overall system. Furthermore, all personal identification information and personal health information for the subject patient(s) is held in other encrypted systems in conjunction with a one-time token use method when data needs to be transferred as requested from the patient held identifier's side.

BRIEF DESCRIPTION OF THE DRAWINGS

FIG. 1 shows an exploded perspective view of one potentially preferred capnography device.

FIG. 2 shows a side perspective view of the capnography device of FIG. 1.

FIG. 3 shows a side perspective view of a capnography device implemented within a CPAP mask.

FIG. 4 shows an exploded perspective view of the entire composite structure of FIG. 3.

FIG. 5 shows a flow chart of the actions undertaken within the capnography device in one possible embodiment of the disclosed system.

FIG. 6 shows a flow chart of the actions undertaken within the base station device in one possible embodiment of the disclosed system.

FIG. 7 depicts a smart sensor capnography chip and ring chamber component as part of one potential embodiment of the inventive capnography device and system.

FIG. 8 shows a potential housing embodiment for combination with the chamber/chip component of FIG. 7.

FIG. 9 depicts the combined chip/housing components for inclusion within a further in-line device for utilization within the overall system.

DETAILED DESCRIPTION OF THE DRAWINGS AND PREFERRED EMBODIMENTS

Figure 10:
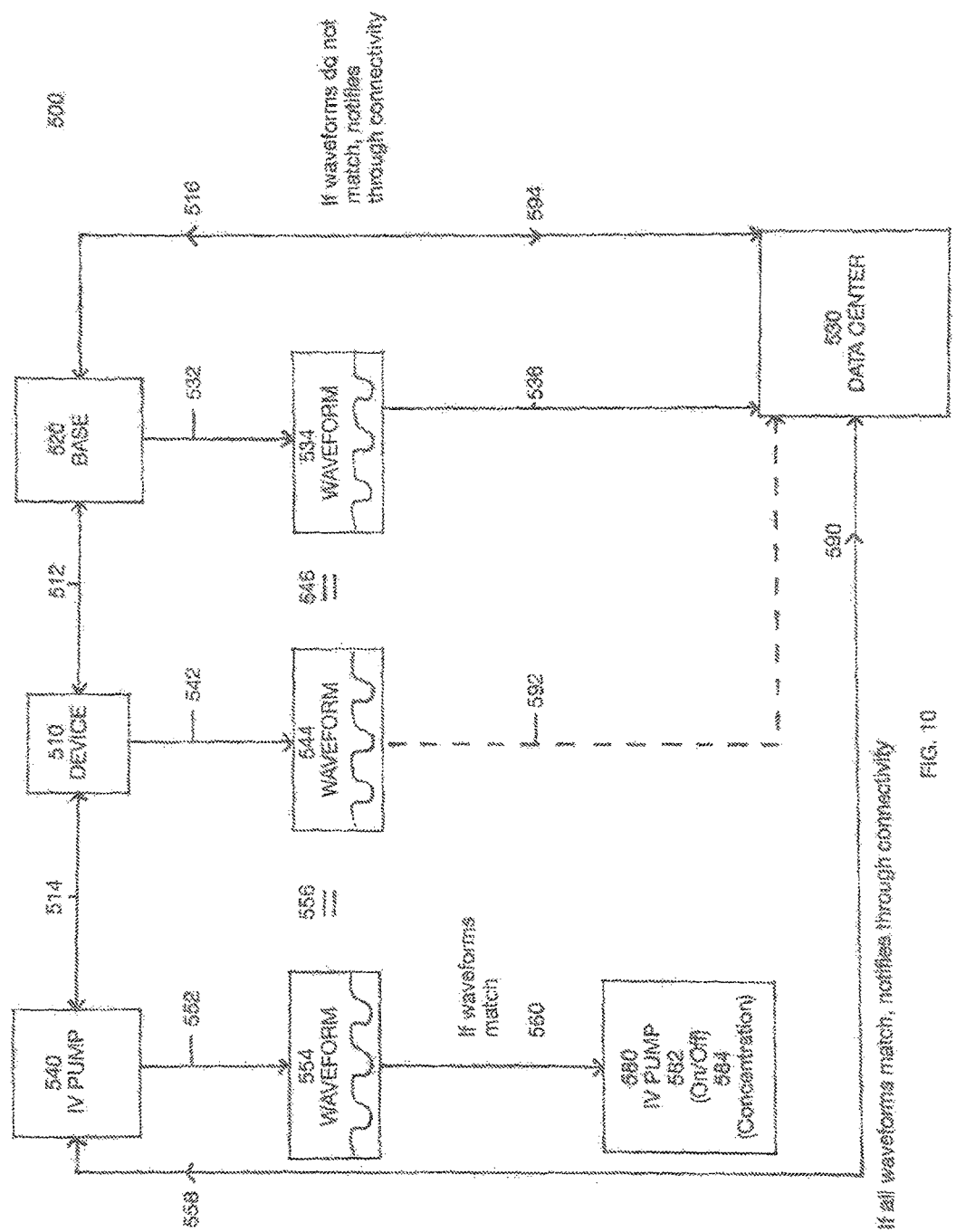
FIG. 10 is a flow diagram showing the operations of the entire capnography/drug delivery system as described herein.

Reference now should be made to the drawings, presented as non-limiting possible embodiments in accordance with the descriptions provided above. The ordinarily skilled artisan would fully understand the breadth and scope intended herein in relation to the following potentially preferred types.

It will be understood that, although the terms first, second, third, etc. may be used herein to describe various elements, these elements should not be limited by these terms. These terms are only used to distinguish one element from another element. Thus, a first element discussed below could be termed a second element without departing from the teachings of the present disclosure.

The terminology used herein is for the purpose of describing particular embodiments only and is not intended to be limiting. As used herein, the singular forms "a", "an", and "the" are intended to include the plural forms as well, unless the context clearly indicates otherwise. It will be further understood that the terms "comprises" and/or "comprising" or "includes" and/or "including" when used in this specification, specify the presence of stated features, regions, integers, steps, operations, elements, and/or components, but do not preclude the presence or addition of one or more other features, regions, integers, steps, operations, elements, components, and/or groups thereof.

FIG. 1 provides an exploded view of a potentially preferred capnography device (10 of FIG. 2). Shown is a top shell cover 1 to provide protection for and over an MCU processor 2 (with, as one non-limiting example a 433 MHz radio component for compilation and communication purposes). A top shell 3 provides a placement location for the processor 2 within a suitably configured recess 3a therein and connects with the top shell cover 1 for such a benefit. A top shell mid cover 4 allows for connection between carbon dioxide sensors 5 and the processor 2 through channels 4a therein. A bottom mid shell 6 structure provides a base location for the carbon dioxide sensor component 5 (including an infrared beam generator 5a and an infrared sensor 5b to detect carbon dioxide levels) with guides 6a for placement of such carbon dioxide sensor components 5 therein in opposite relation and attachment with the top middle shell 4. The top middle shell 4 includes a top archway 4b and the bottom mid shell 6 includes a bottom archway 6b in order to form, upon attachment of the two shells 4, 6 and opening (12 in FIG. 2) that provides the channel for a patient to breath into for collection and measurement of carbon dioxide levels. A bottom shell 7 is further provided to support a battery 8 (such as, without limitation, a 7-volt LiPo type, although any like rechargeable battery implement may be utilized for such a purpose). The bottom shell 7 thus includes a recess 7a for such battery 8 placement with a bottom shell cover 9 provided to protect and cover the battery 8 in much the same way the top shell cover 1 provides such benefits for the processor 2. Thus, in FIG. 2 it is shown the total composite capnography device 10 with the aforementioned breathing channel 12 to capture and measure carbon dioxide levels. In this manner, the patient (not illustrated) directs his or her expelled breath through such a channel 12 in order for the carbon dioxide sensor components 5 to detect such levels and record microvoltage changes in relation to the concentration of carbon dioxide present within such a channel at any given time. The infrared beam generator 5a supplies a laser to traverse the channel to the infrared sensor 5b, thereby allowing for infrared beam distortions to be detected in relation to such carbon dioxide levels (and measured initially as, again, microvoltage levels that change due to infrared beam signal capture over time). The battery 8 supplies sufficient power for the infrared beam generator 5a to operate and the infrared sensor 5b to record such levels. The battery 8 is connected with a switch (not illustrated)

situated in proximity to the carbon dioxide sensor components 5 in order to control activation and deactivation thereof as programmed within the processor 2. As the processor 2 sets the definitive program for such series of controls, the infrared beam generator 5b can be controlled for prolonged life in order to at least reduce the tendency for replacement due to burn out, particularly since such infrared beams require relatively high power for operation. To that end, such power up/power down capabilities may be structured for cycles of anywhere from 10 milliseconds to 10 seconds, if desired. The only limitation to such cyclical activity being the ability provided through the processor 2 in terms of its own speed for reaction times to compile and record the results from such carbon dioxide level measurements. The processor 2 further receives the microvoltage change measurements from the infrared sensor 5b directly and compiles such results through a suitable algorithm to generate a capnograph (not illustrated) that is then compared with high and low limits of acceptable recorded carbon dioxide respiratory levels. If the level is too low (indicating ineffective oxygen intake and/or ineffective respiration capabilities) or too high (indicating ineffective ability of the target patient to expire carbon dioxide during respiration), the processor 2, subsequent to capnograph generation, records and alerts the target patient (and any other caregiver, selected associate to such patient, and the like) of such a result. Such an alert may be provided immediately or in response to continued measurements within a certain time frame (for example, too high a level for such a specific target patient for more than 10 seconds or, with 10 millisecond cycles, for more than 75% of a 100 sequential cycle series, again, of course, without limitation; the same may be true and followed for too low a carbon dioxide measured level within the algorithm of the processor 2, as well, again, though, without limitation) such that even if a target patient has lost consciousness, the system utilizing the capnography device 10 provides constant surveillance and monitoring to alert needed individuals and/or medical professionals to provide immediate (or at least as soon as possible) attention. As discussed above, the processor 2 within the device 10 allows for such instant compilation of data and alert capabilities if needed. The alert provision is permitted through the communication platform (radio, for example, without limitation, present in relation to the processor 2) that sends to a base and/or data center (not illustrated) that sends to such individuals and/or medical professionals as necessary (and as provided within the programmed system itself). Upon such alert, as noted above, the data center (not illustrated) includes a processor (not illustrated) with the same algorithm to compile transferred data from the capnography device 10 in order to generate a capnograph readout on demand for further review and consideration by a medical professional. With the wireless capabilities provided by the disclosed capnography device 10, comfort and versatility is provided for such respiration monitoring purposes that have heretofore been nonexistent within the medical field and other areas.

As alluded to above, the utilization of such a capnography device 10 may be introduced within any type of system, overall device, environment, etc., that permits such constant surveillance and monitoring of a person, patient, or both, in relation to the quality (and quantity, if desired) of his or her respiratory activity. Thus, this device 10 may be introduced within a SCUBA system, an airplane pilot monitor, a military soldier monitor, a gas mask system, a firefighter mask system, an oxygen mask (or nares tubing device) system, and the like. FIGS. 3 and 4 show one possible embodiment of such an overall system with a CPAP mask 100 including a capnography device 130 therein for patient monitoring purposes. The CPAP mask 100 includes a mouth and nose cover 120 that houses a remote, wireless capnography device 130. Such a capnography device 130 includes a channel 130a aligned with the user's mouth and nose to receive expressed air (carbon dioxide, as one gas, of course) for measurement purposes. A hose 140 leads to the mouth and nose cover 120 for supply of oxygen, as well. FIG. 4 shows the exploded view of the capnography device 130 present within the mouth and nose cover 120 of the CPAP mask 100. In this iteration, there is present a top shell cover 150 with a recess 150a for the presence of the carbon dioxide sensor components 200 (infrared beam generator 200a and infrared sensor 200b). A bottom shell cover 500 is provide with a battery recess 500a and a processor recess 500b, as well as towers 500c for carbon dioxide sensors 200 alignment (again they are opposite one another with a channel 130a created by such towers 500c). The processor 400 is provided as above and the battery 300 as well. Again, cycles of power up and power down allows for generation and measurement of carbon dioxide levels that are compiled by the processor 400 to allow for surveillance and monitoring as needed with the same alert capabilities as described above, as well.

FIG. 5 shows a flow chart for one possible embodiment of the overall system directed to the capnography device components thereof. FIG. 6 show a possible embodiment of the remainder of the overall system. These steps include the cyclical method of collecting data pertaining to a patient/individual's respiratory status (carbon dioxide exhalation levels) through initial power up of the infrared source and sensor by the MCU 210 (also referred to as I1 for verification purposes), initializing the sensor to collect data from the IR beam 212, having an established instant with both beam and sensor in operation 213, collecting measurements in terms of the carbon dioxide "obstructions" of the IR beam (thus indicating concentration of carbon dioxide per voltage changes at the IR sensor level) 214, filtering such measurements to proper levels 216, accumulating the collected data and transferring continuously to the MCU 218 (with the time such transfer begins as D1, and including the amount of data transferred, as well), determining if more data is needed within that cycle 220, particularly in response to a lack of data transferred or if the amount transferred is below a threshold to meet a certain parameter for alarm generation purposes, where if more is needed (YES) then the system returns 222 to the sensor/beam establishment for continued measurements 213, (with any further return potentially causing the device to determine a problem exists with the device or the patient/individual's respiratory status, thus necessitating alarm code generation) and then continuing through the steps 214, 216, 218, 220 until all such cycle data generation and capture has occurred (220 N), providing a set amount of data transferred during each cycle from the sensor to the MCU. At that point, the MCU may compile the raw data through the algorithm to determine if carbon dioxide parameters are met, exceeded, or too low for alarm purposes. If such parameters are not met for a set amount of time, then the MCU sends the necessary alarm code in relation to the parameter deficiency(ies) as well as further raw data packets 224 to the base station, the data center, the patient, health care provider(s), monitoring individuals, emergency medical personnel, and/or selected individuals (family members, for example), wherein such alarms are communicated through any or all of the available communication protocols present within the capnography device, the base station, and/or the data center (thus, through RFID with an interrogation from the base station, through wireless system, through Bluetooth, and/or through cellular platform). Such raw data packet transfers thus provides the unprocessed data to be sent to different receivers for not only compilation and monitoring of the patient/individual's respiratory status subsequent to alarm generation of a problem situation, but also allows for such an algorithm at such different locations (again, such is the same algorithm in each place and instance) to verify such raw data is proper and reliable prior to such processing. The steps above 212 (I1), 214 (D1) provide specific times during each cycle that are pre-set prior to each cycle, thus allowing for the algorithm to check each data packet for such values. If any value is off, then the system determines a problem has occurred, whether in terms of sensor or IR source problems and/or defects, MCU problems and/or defects, power switch problems and/or defects, and/or compromised raw data (hacking). The presence of data that exceeds the set amount required during transfer from sensor to MCU indicates a hack has most likely occurred, for instance. In such a situation, the algorithm will not permit compilation of data and will prevent any processing thereof, thus curtailing any potential threat to the software and/or hardware of the device and connected communication receivers associated therewith. In any event, upon receipt by the MCU 220 N, such raw data is initially compiled to determine the possible alarm status for the patient/individual. If the alarm does sound, as noted above, then such raw data is not only collected at the MCU but sent to the other devices for further verification overall that the raw data is reliable, but also to allow ultimately for the recipients to continuously monitor the patient/individual after the initial respiratory status issue (alarm) has happened. With the initial MCU receipt and compilation of raw data from the sensor, the algorithm therein compiles such data in relation to the time initiated, the time transferred from the sensor, the time such transfer is completed (within each cycle), and the amount of data transferred within the timeframe specified, processing the data to create a continuous waveform for assessment of parameters of carbon dioxide levels, and notifying (through an alarm) if such measurements fall outside set maxima and minima, again, as alluded to above. Additionally, and as discussed above, the overall system is provided with such specific raw data values such that the mirrored algorithm (i.e., algorithm that is the same within each described device) utilized therein exhibits the capacity to continue searching for any missing raw data portion within a data packet prior to compilation and processing as such values as noted above must be filled within each data packet response prior to such action. Thus, unlike UDP protocols, which will ignore missing data and simply move forward without such data present, leaving compromised data a distinct possibility, at least, this system provides a manner of allowing for simple search and locate of each data packet portion to ensure reliability overall prior to any processing of such raw data at any device.

FIG. 6 thus shows the method steps within the overall system undertaken at the base station, as one example, and as further discussed below. These steps include the initial power up of the station (or other device, including the data center and smartphones, etc., of specified pre-set recipients of such information) 310 (again, with such an external location, considered as I1 for data verification purposes) which occurs automatically upon receipt of communication from the device MCU. At this point, there are two different pathways 312, 314 depending on the manner of raw data transfer from the capnography device 224 (either of which leads to receipt of transferred data considered as D1 at such a location with the amount of data transferred as part of the D1 value, as noted above). The first involves the wi-fi and/or Bluetooth and/or cellular communication alternative(s) 313 that receive such transferred raw data and move to an establishment point 330 in relation to further steps. The system at the base station (or other device) then determines if any requests for compilation by the algorithm have been received from the capnography device 332. If not, then the system returns back 334 to the establishment point 330 to await anything further subsequent to power up 310 and communication initiation 313. If the request(s) is/are received 332 Y, then the system proceeds to accept the accumulated raw data from the MCU 336 and compile at the algorithm level to verify such data is true and to generate the continuous waveform as data is received and authorized for processing. Once that is accomplished, the response packet is sent to the data center 338 for further processing, as well as any other pre-selected recipient. The system then returns 340 to the establishment point to await the next data packet transfer and to undertake the same steps again. Simultaneously, the base station undertakes initiation of the RFID reader 316 to await response from an interrogation generated thereby and sent to the capnography device RFID tag. Upon establishing such has been initiated 318, the base determines if any requests of this type with raw data from the capnography device have been received 320. If not, then the system returns 322 to the establishment point 318. If yes 320 Y, then the system appends such raw data to a reading buffer for algorithm submission and compilation as above. Once concluded, the system returns 326 to the establishment point 318 to undertake the next submitted raw data through this pathway 314. This further step is of utmost importance for a number of reasons, including, without limitation, providing raw data thereafter via any communication protocol present (RFID tag, wi-fi, Bluetooth, and/or cellular) to any or all of the base station, the data center, and selected recipients (doctor, relative, etc.) for further monitoring and waveform generation (with the algorithm used within the capnography device MCU also present within each of such recipients' system for verified data transfer and reception and, upon verification of reliable data transfer, processing thereof to create such a continuous waveform) for further monitoring and surveillance unless and until such patient/individual is treated/rescued/etc. and such capnography system is not necessary any further. Thus, even though such data transfer from capnography device to base station may actually be provided to the data center and other recipients (as noted above) directly from the capnography device itself, the system may also have the initial transfer of raw data to the base station first and then transferred to the data center, recipients, etc., thereafter (and may be from data center to recipients or from base station to data center and recipients simultaneously). Such raw data transfer and treatment at these various locations is also, as noted previously, essential to ensure the raw data itself is verified and completely reliable prior to processing by any processing component (whether at the base, the data center, or with any recipient's own device. Thus, the steps in FIG. 6 may be considered as if such has occurred within the data center or systems of such selected recipients separately or as well.

As an alternative device, then is the smart sensor capnography chip type shown in relation to FIGS. 7 through 9. A ring chamber 400 (such as a hollow ring/tube for attachment within an intubating tube, as one non-limiting example) is provided with a smart sensor miniaturized chip 410 as described above (including the IR source and IR sensor component; not illustrated). FIG. 8 shows the separate (but connectable) housing 420 including a connectivity component 422 (Bluetooth, Wi-Fi, cellular components, at least), an RFID tag 424, an MCU components 426, and a power module 428. Additionally, the housing 420 including a base structure 432 that holds a connection data chip 430 for storage of raw data from the smart sensor chip (410 of FIG. 7) and transfer to the MCU 426 for utilization thereof (determination of respiratory status for surveillance and notification purposes, as described above). Thus, as connected (such as snapped together, as one non-limiting possibility) the full capnography (smart sensor chip/housing) device 440 includes all such components with the smart sensor chip 410 aligned, if needed, with the data storage chip 430. The ring chamber 400 thus provides the shape and area to capture, momentarily, as needed, the target patient/individual's exhaled breath to provide a continuous and constant measure of carbon dioxide concentrations therein via the IR source/sensor on/within the smart sensor capnography chip 410 which transfers to the data storage chip 430 which then transfers to the MCU 426 for processing for alarm purposes, again, as noted above and throughout, above. Thus, differently sized devices may function in such a capacity for remote surveillance and notification possibilities in a constant and continuous manner.

This overall system thus provides an overarching method for reliably collecting carbon dioxide exhalation measurements through a wireless, remote device and monitoring continuously the levels generated and captured thereby for any abnormalities. With this wireless, remote capability, comfort and safety are optimized with the ability to further provide reliable raw data from the capnography device itself for surveillance purposes, allowing for reliable notifications to be provided to any selected recipients of any measurements that show excess or too low carbon dioxide emissions from the patient/individual, and further monitoring thereafter until proper treatment can be provided. This system removes the typical cumbersome wired monitoring devices that are limited to hospital settings, allowing for such respiratory surveillance capabilities in any setting that permits wireless communications. The data integrity aspects of this overall system thus also provide a reliability level prior to data processing that has heretofore been nonexistent not only within the capnography art, but the medical field as well.

FIG. 10 depicts a diagram 500 of a potentially preferred embodiment of the completely wireless capnography/drug delivery system (meeting all ISO 11073 standards) described within this disclosure. Such a system has a capnography device 510, a drug delivery device 540 (here provided as an IV pump, but to be understood to unclude any programmable drug delivery device as described above, including for pharmaceuticals, gases, antidotes, and the like), an external connectivity base 520, and a data center 530. Each component device 510, 520, 530, 540 has its own mirrored algorithm (capnography waveform generating algorithm, again, as described in detail above)(not illustrated). The capnography device 510, as above, is utilized to monitor the carbon dioxide concentrations of a subject patient respiratory gases with intermittent data capture and transfer 542 for capnography device capnography waveform generation 544 (through the algorithm). If such waveform results are outside subject patient parameters (again, as above), an alarm code is generated and all subsequent raw capnography sensor data is transferred 512 to the external connectivity base 520, transferred 514 to the drug delivery device 540, and, possibly, transferred 592 to the data center 530. The algorithms within each component 520, 530, 540 then receive such raw data (in encrypted format which must be decrypted for processing at each device; if such decryption fails, then the system considers any discprenacy to indicate a corruption, compromise, or other improper situation, such as a hack, etc., of the system within the component device at issue), transfer to each individual algorithm 532, 552, and generate separate waveforms therefrom 534, 554 to generate alarm codes to compare 546, 556 (with the capnography device waveform alarm code from the same raw data, as well) to determine if all raw data as transferred is in proper form and thus the devices are all functioning properly, as well as to monitor the subject patient in relation to such capnography measurements and results. If such waveforms all match, then the drug delivery device determines how the results affect said subject patient's needed drug delivery 560. If needed, the data center 530 can further provide directive 558 to the drug delivery device 540 to proceed with delivery operation modifications 582, 584. Thus, if the drug delivery device is currently in operation or primed to start up on command 580 and delivering needed medicaments, gases, pharmaceuticals, antidotes, and/or any combinations thereof, then the instructions within the drug delivery operating system as to measured capnography waveform results indicates whether to activate or deactivate 582 (to initiate new levels of or discontinue drug delivery) or adjust concentrations 584 of delivered drug (increase or decrease, for instance). Thus, as noted previously, in relation to the wireless capabilities of the overall system, capnography device 510 and drug delivery device 540 may actually be provided on the person of the subject patient in order to allow for continued monitoring and surveillance with complete mobility and freedom, as well. The external connectivity base provides the needed power transfer capability, as noted above, as well as extra check for system functions (and possible notifications of other entities if an alarm code is generated). The data center provides a means to communicate, as well, with other entities (physician, hospital, loved one) and providing transfer to an EMR, if desired, as well. Of course, the drug delivery device, typically including a preliminarily embedded Bluetooth or like accessory for EMR communication purposes, may also provide notifications directly to such an EMR in relation to alarm code generations within the overall system, too.

Additionally, FIG. 10 provides an overview of the system 500 as it allows for further checks between the drug delivery device 540 and the capnography device 510, at least. As noted above, raw data bursts may be transferred 514 from capnography device 510 to drug delivery device 540 (and, alternatively, if desired, to the external connectivity base 520 and data center 530, as well) at pre-set intervals (for example, without limitations, every 15 minutes, every 30 minutes, every hour, and the like, as desired) and for pre-set duration periods (such as, without limitation, for 30 seconds, 1 minute, 2 minutes, and the like, as desired) in order to provide an indication within the system that first, the capnography device is at least functioning to deliver such bursts, and secondarily, to allow the drug delivery operating system capnography waveform generating algorithm to generate waveforms during such pre-set duration periods to assess if the capnography device is functioning properly in terms of alarm code generations. If such a waveform (or, actually multiple waveforms) generated by the drug delivery operation system algorithm shows results that are outside set parameters for the subject patient, and no alarm code has been or is then generated by the capnography device itself, the system can be properly and immediately updated and notifications provided that corrections are necessary (such as, for instance, possible power transfer due to low power levels, corruption of raw data, and other possible issues). In such an instance, the drug delivery device 540, the external connectivity base 520 notifies the data center 590, 594 (and possibly the capnography device 510 notifies 592) of any such problems for notifications to then be provided as needed for immediate corrections, as well.

Overall, then, the system allows for the conditions and results as noted previously, particularly the ability to provide a mobile, portable, capnography/drug delivery device that operates with complete checks to assure and ensure that any delivered pharmaceutical, gas, antidote, medicament, or combinations thereof, are appropriately and properly delivered for a subject patient in relation to measured capnography waveform results thereof. Thus, without limitation, such a system may be employed at a subject patient's home with full mobility and no need for being tied to rolling IV towers, wall-mounted (or the like) gas tanks, and the like, permitting, as well, the ability to travel outside a home, too, with directed drug delivery for optimal effect. Thus, the capnography device may be provided as a structure as noted above (mask, neck-borne device, etc.) and the drug delivery device may be supplied on a subject patient's body, clothes, within a carrying case, and the like, as well. Such a system may thus be employed, additionally, for military personnel on the battlefield, with IV delivery, analgesic delivery, oxygen gas delivery, even possible poisonous substance and/or gas antidote delivery, without limitation, of course, to best ensure full mobility and safe medical concerns for such individuals (not necessarily patients, of course, but in a proactive sense such a drug delivery system may be provided in relation to carbon dioxide respiratory concentrations). Basically, such a mobile, portable, safe, effective, and hack-proof system allows for medical industry improvements that have heretofore been unexplored.

Having described the invention in detail it is obvious that one skilled in the art will be able to make variations and modifications thereto without departing from the scope of the present invention. Accordingly, the scope of the present invention should be determined only by the claims appended hereto.

What I claim is:

1. A capnography monitoring, notification, analysis, and drug delivery system for an individual person comprising
a) a capnography device having an exhalation capture passage; an infrared source providing an infrared beam through said passage; an infrared sensor aligned opposite said infrared source to detect voltage variations associated with carbon dioxide concentrations, inspiration length, and expiration length within said individual's captured respiratory status; a microcomputer (MCU) programmed with a capnograph waveform generating algorithm; at least one radio frequency identification (RFID) tag; an optional data storage component other than said microcomputer; and a communication component including a WIFI antenna, a Bluetooth antenna, and, optionally, a cellular communicator;
b) an external connectivity base comprising an inductive coupling component associated with said capnography device, a receiver component for reception of communicated information from said capnography device, a computer processor, and an information transfer component, wherein said external connectivity base computer processor is programmed with the same waveform generating algorithm as the capnography device;
c) a data center comprising a rules engine, and a data center computer processor, wherein said data center computer processor is programmed with the same waveform generating algorithm as the capnography device; and
d) at least one drug delivery device having an operating system programmed with the same waveform generating algorithm as the capnography device, wherein said at least one drug delivery device is automated, and wherein said drug delivery device operating system is further programmed with capnography waveform parameters associated with a drug for treatment of a subject patient therewith in relation to utilization of said capnography device;
wherein said algorithm programmed within said capnography device, said external connectivity base, said data center, and said drug delivery device operating system compiles infrared sensor measurements from said infrared sensor to generate a capnograph waveform associated therewith,
wherein said capnography device MCU further includes pre-set parameters associated with certain maximum and minimum carbon dioxide measurement concentrations, inspiration length measurement durations, and expiration length measurement durations as captured by said infrared sensor and compiled by said algorithm in a waveform,
wherein, if at any time during utilization by said individual, said parameters are exceeded in terms of said maximum or below said minimum carbon dioxide concentrations for a pre-set continuous amount of time, then said capnography device MCU generates an alarm code associated specifically with said waveform measurements for communication and immediate notification to pre-selected parties as to a condition of said individual in relation to said exhalation carbon dioxide concentration measurements,
wherein, upon such a notification action, said capnography device continues to capture carbon dioxide exhalation concentration measurements as raw data with transfer of said raw data from said capnography device MCU to at least one communication component of said at least one RFID tag, Bluetooth antenna, WIFI antenna, and/or cellular communicator for continuous transfer to at least said drug delivery device operating system and said external connectivity base, and, alternatively, also to said data center, and said capnography device MCU further generates said alarm code within said capnograph waveform generating algorithm therein as an indicator of a situation pertaining to said alarm generation,
wherein said continuous transfer to said drug delivery device operating system and said external connectivity base and/or said data center is undertaken for transfer of the alarm situation whether in terms of patient/individual respiratory status or capnography device status via compilation of said continuously transferred raw data within said capnograph generating algorithm and verification and processing thereof;
wherein said drug delivery device operating system is further programmed to provide delivery operation modification of said drug in response to said alarm code generation at said capnography device upon transfer, receipt, verification, and processing of said raw data from said capnography device MCU and generation of said waveform by said drug delivery device operating system capnography waveform generating algorithm such that any resultant waveform levels outside said parameters associated with said drug for said subject patient causes a drug delivery operation modification in response thereto, wherein said drug delivery operation modification is selected from the activities of activating said device, deactivating said device, increasing flow of drug delivery by said device, decreasing flow of drug delivery by said device, increasing concentrations of drug within flow delivery by said device, decreasing concentrations of drug within flow delivery by said device, and any combination or combinations thereof;

wherein said capnography waveform generating algorithm located within all of said capnography device, said external connectivity base, said data center, and said drug delivery device operating system are configured to receive the same raw data from said capnography device and thus generate, as needed, the same capnography waveforms at all such locations, allowing for complete comparisons to assure said raw data and said capnography waveforms are proper; wherein said capnography device further receives power from and transfers information directly to said external connectivity base through said inductive coupling component upon placement of said capnography device within a certain proximity thereto of said external connectivity base; and wherein said inductive coupling is further configured to provide raw data transfer and alarm code notification to said external connectivity base upon discovery of defect within said capnography device for possible remedy thereof.

2. The system of claim 1 wherein said drug delivery device is selected from a programmable pump, a programmable ventilator, and any combination thereof.

3. The system of claim 2 wherein said drug delivery device is at least one programmable pump associated with an internal drug delivery line selected from the group of consisting of at least one intravenous line, at least one feeding tube, at least one epidural line, at least one patient-controlled analgesia line, and any combination or combinations thereof.

4. The system of claim 2 wherein said drug delivery device is at least one programmable ventilator selected from the group consisting of a CPAP machine, a BIPAP machine, a mechanical ventilatory assistance device, and any combination or combinations thereof.

5. The system of claim 1 wherein if any parameters fall outside acceptable levels for longer than a predetermined time duration, then said algorithm generates said alarm code, wherein said alarm code causes certain activities within the overall system to subsequently occur including:

a) notification if such data indicate said individual requires immediate attention and/or said device requires remedy for problems or defects therein, b) continuous transfer of collected raw data from said MCU to pre-selected external locations that utilize the same capnography waveform generating algorithm programmed within said capnography device MCU, and c) synching all of said programmed capnography waveform generating algorithms within said pre-selected external locations for data reception, verification, and processing thereof to generate a continuous waveform at each of said locations in relation to said subject individual's respiratory status;

wherein such verification provides block chain capability within said system for complete reliability of data.

6. The system of claim 1 wherein said data center is further configured to verify said raw data by generating a block chain result.

7. The system of claim 1 wherein said drug delivery device operating system capnography waveform generating algorithm is programmed to receive pre-set time interval-based raw data bursts of pre-set duration from said capnography device, wherein said raw data bursts provide indication of capnography device operation for assessment of proper activity of said capnography device, wherein if said data bursts are not received at said pre-set time interval or outside a period of said pre-set duration, then said drug delivery device operating system capnography waveform generating algorithm generates an alarm of improper capnography device operation for transfer to said external connectivity base and, if utilized, said data center, wherein if said raw data bursts are properly received at said pre-set time interval and for said duration, then capnography device operations are deemed proper and the system proceeds as programmed, wherein if said raw data transferred through said raw data bursts from said capnography device are properly received at said time interval and for said duration and are processed by said drug delivery device operating system capnography waveform generating algorithm and said results thereof fall outside subject patient parameters without an alarm notification from said capnography device, then said drug delivery device operating system notifies said external connectivity base and, if utilized, said data center that said capnography device is not operating properly and said drug delivery device is configured to activate said drug delivery operation modification to ensure proper delivery of needed drug in response to said drug delivery device operating system capnography waveform generating algorithm results.

8. The system of claim 7 wherein said capnography device is configured to transfer said raw data burst at said pre-set time interval and for said time duration to said external connectivity base and said drug delivery device operating system at the same time.

* * * * *